(12) United States Patent
Izraeli et al.

(10) Patent No.: US 8,679,484 B2
(45) Date of Patent: Mar. 25, 2014

(54) METHOD FOR REMOVAL OF TOXINS FROM MUCOSAL MEMBRANES

(75) Inventors: Tomer Izraeli, Rishon Lezion (IL); Smadar Cohen, Beer-Sheva (IL); Robert S. Marks, Omer (IL)

(73) Assignee: Polyrizon Ltd., Rishon Lezion (IL)

(*) Notice: Subject to any disclaimer, the term of this patent is extended or adjusted under 35 U.S.C. 154(b) by 237 days.

(21) Appl. No.: 11/885,340

(22) PCT Filed: Mar. 2, 2006

(86) PCT No.: PCT/IL2006/000291
§ 371 (c)(1),
(2), (4) Date: Nov. 1, 2007

(87) PCT Pub. No.: WO2006/092799
PCT Pub. Date: Sep. 8, 2006

(65) Prior Publication Data
US 2008/0317765 A1    Dec. 25, 2008

Related U.S. Application Data

(60) Provisional application No. 60/657,388, filed on Mar. 2, 2005, provisional application No. 60/738,973, filed on Nov. 23, 2005.

(51) Int. Cl.
*A61K 39/00* (2006.01)
*A61K 39/395* (2006.01)

(52) U.S. Cl.
USPC .................................. 424/130.1; 424/178.1

(58) Field of Classification Search
None
See application file for complete search history.

(56) References Cited

U.S. PATENT DOCUMENTS

| 4,900,552 A | 2/1990 | Sanvordeker et al. |
|---|---|---|
| 5,670,626 A * | 9/1997 | Chang .................. 530/388.5 |
| 5,879,710 A | 3/1999 | Bromet |
| 5,900,247 A | 5/1999 | Rault et al. |
| 5,925,534 A | 7/1999 | Miki et al. |
| 5,942,243 A | 8/1999 | Shah |
| 6,849,259 B2 * | 2/2005 | Haurum et al. ............ 424/171.1 |
| 2005/0281775 A1 | 12/2005 | Carrington et al. |

FOREIGN PATENT DOCUMENTS

EP    1 243 256    9/2002

OTHER PUBLICATIONS

Albarghouthi, et al., Immobilization of Antibodies on Alginate-Chitosan Beads, Int. J. Pharmaceut., 2000; 206:23-34.*
Kurucz et al. 'Current Animal Models of Bronchial Asthma.' Curr. Pharm. Des. 12:3175-3194, 2006.*
Zheng et al. 'The Atopic March: Progression from Atopic Dermatitis to Allergic Rhinitis and Asthma.' Allergy Asthma Immunol Res. 3(2):67-73, 2011.*
Gombotz et al. 'Protein release from alginate matrices.' Advanced Drug Delivery Reviews 31:267-285, 1998.*
Gavini, E., et al., "Mucoadhesive Vaginal Tablets as Veterinary Delivery System for the Controlled Release of an Antimicrobial Drug, Acriflavine", *AAPS PharmSci*, p. No. 1-7, (2002).
Valenta, C., "The Use of Mucoadhesive Polymers in Vaginal Delivery", *Advanced Drug Delivery Reviews*, vol. No. 57, p. No. 1692-1712, (2005).
Ugwoke, M., et al., "Nasak Mucoadhesive Drug Delivery: Background, Applications, Trends and Future Perspectives", *Advanced Drug Delivery Reviews*, vol. No. 57, p. No. 1640-1665, (2005).
Albarghouthi, M., et al., "Immobilization of Antibodies on Alginate-chitosan Beads", vol. No. 206, p. No. 23-34, (2000).

* cited by examiner

*Primary Examiner* — Nora Rooney
(74) *Attorney, Agent, or Firm* — Browdy and Neimark, PLLC

(57) ABSTRACT

The present invention provides novel mucoadhesive compounds useful in the prevention of diseases and disorders of or which are associated with the mucosal membrane.

11 Claims, 9 Drawing Sheets

Semi - Loaded Ligand

Semi - Loaded Ligand

Fully - Loaded Ligand

METHOD FOR REMOVAL OF TOXINS FROM MUCOSAL MEMBRANES

CROSS-REFERENCE

This is a National Phase Application filed under 35 U.S.C. 371 of International Application No. PCT/IL06/000291, filed Mar. 2, 2006, claiming the benefit under 35 USC 119(e) of U.S. Provisional Application No. 60/657,388, filed Mar. 2, 2005, and claiming the benefit under 35 USC 119(e) of U.S. Provisional Application No. 60/738,973, filed Nov. 23, 2005, the entire contents of each of which is hereby incorporated herein by reference in its entirety.

FIELD OF THE INVENTION

This invention relates to a method for removal of toxins from mucosal membranes.

BACKGROUND OF THE INVENTION

The mucosal membrane or tissue is a mucus-secreting membrane which lines all body cavities or passages that communicate with the exterior. While bioadhesion refers to the ability of certain synthetic and biological macromolecules and hydrocolloids to adhere to biological tissues, mucoadhesive compounds are capable of adhering to mucosal membranes (mucosal tissues) through a complex phenomenon, which in part depends upon the properties of compound, biological tissue, and the surrounding environment. Several factors have been found to contribute to a compound's bioadhesive capacity: the presence of functional groups able to form hydrogen bridges, the presence and strength of anionic charges, sufficient elasticity for the polymeric chains to interpenetrate the mucous layer, and high molecular weight. For this reason, most mucoadhesive compounds are polymeric.

Mucoadhesive drug delivery systems exploit the attraction between the mucus and polymeric drug carrier. They provide localization of the carriers within the specific site and prolonged residence time of the delivery devices. These greatly enhance the bioavailability of the drugs, especially in the case of peptide and protein delivery. Such systems have been used in dentistry, orthopedics, ophthalmology, and in surgical applications and recently with the emergence of controlled release systems for local release, such applications include also systems for release of drugs in the buccal or nasal cavity, and for intestinal or rectal administration.

Mucoadhesive vaginal formulations have also been disclosed for example by Gavini et al (Mucoadhesive vaginal tablets as veterinary delivery for the controlled release of an antimicrobial drug, acriflavone: AAPS PharmaSci 2002; 3(3) article 20) and C. Valenta (The use of mucoadhesive polymers in vaginal delivery: Advances Drug delivery Reviews 2005: 57, 1692-1712). Nasal drug delivery using mucoadhesive carrier has also been described (Nasal mucoadhesive drug delivery: Background, applications, trends and future perspectives: Ugwoke et al., Advanced Drug Delivery Reviews 2005; 57, 1640-1665).

US application no. 2005/0281775 discloses a method for augmenting an epithelial mucosal barrier by contacting the barrier with a topical composition which comprises a mucoadhesive polymer. The method and compositions discloses are said of being useful in improving mucosal barrier function by, for example, topical application to an exposes or injured epithelial surface or by coating a compromised mucosal barrier in inflammatory bowel disease.

SUMMARY OF THE INVENTION

It has been found in accordance with the present invention that mucoadhesive systems may be utilized not only for the delivery of pharmaceuticals and other active agents into the mucosal membranes or mucosal tissues, as shown extensively by existing prior art, but also remove therefrom toxins which can cause allergies and other deficiencies. The removal of such toxins from the respiratory system, for examples, may be achieved by binding one or more of said toxins to novel mucoadhesive ligand systems. Such systems may thus find utility as therapeutics as well as agents for hygienic and prophylactic purposes.

Thus, in one aspect, the present invention provides a compound of the formula $A\text{-}(B)_n$:

wherein A is a mucoadhesive backbone, B is a ligand group being chemically substituted to A and capable of interacting with a toxin, and n is the number of ligand groups chemically substituted to said A, being greater or equal to 1.

The "mucoadhesive backbone", A, is the matrix, chain, polymer or other chemical entity to which the ligand groups, B, are substituted. Backbone A may be biodegradable or non-biodegradable in nature and may be selected based on several parameters such as their intended use and targeted mucosal membrane. Such backbone may be organic, namely substantively composed of carbon atoms; inorganic such as a silica backbone; or a mixture of both. The mucoadhesive backbone may be selected from the group of natural or synthetic (or combination thereof) polymers, metalopolymers, crosslinked polymers, polysaccharides, organic-inorganic polymers, and peptides. The backbone may additionally be charged, i.e. may be presented as a salt.

The polymeric mucoadhesive backbone may be an anionic polymer such as poly(acrylic acid), carrageenan, carbopol, polycarbophil, poly(methacryl acid), alginate, carboxymethylcellulose, sodium hyaluronate; cationic polymer such as chitosan; non-ionic polymer such as hydroxymethylcellulose, hydroxypropylcellulose, polyvinylpirrolidone, polyethyleneglycol; or thiolated polymer such as cysteine conjugates of poly(acrylic acid), polycarbophil and sodium carboxymethylcellulose, 2-iminothiolane chitosan. Additional examples of mucoadhesive polymers are tamarind seed polysaccharide, gelatin, gliadin, pectin, poly-N-vinylpyrrolidone, xanthan gum, and 2-acrylamido 2-methylpropane-sulfonic acid.

The polymers may be homopolymer, copolymer, terpolymer, or interpolymer. These polymers are preferably ionic, and are selected from polycarboxylic acids, polysulfonic acids, or salts thereof. Polysulfonic acids include sulfoethylmethacrylate, sulfopropyl methacrylate, sulfopropyl acrylate, N,N-dimethyl-N-methacryloxyethyl-N-(3-sulfopropyl) ammonium betaine, itaconic acid-bis(1-propyl sulfonizacid-3)ester dipotassium salt and methacrylic acid amidopropyl-dimethyl ammonium sulfobetaine.

Examples of acrylic acid or polyacrylic acid polymers include those having monomers of methyl acrylate, ethyl acrylate, propyl acrylate, isopropyl acrylate, butyl acrylate, isobutyl acrylate, methyl methacrylate, methyl ethacrylate, ethyl methacrylate, octyl acrylate, heptyl acrylate, octyl methacrylate, isopropyl methacrylate, 2-ethylhexyl methacrylate, nonyl acrylate, hexyl acrylate, n-hexyl methacrylate, and the like. Higher alkyl acrylic esters are decyl acrylate, isodecyl methacrylate, lauryl acrylate, stearyl acrylate, behenyl acrylate and melissyl acrylate. Mixtures of two or three or more long chain acrylic esters may be successfully polymerized with one of the carboxylic monomers.

Specifically preferred mucoadhesive polymers are sodium alginate, Chitosan, Chitosan modified with thioglycolic acid (TGA) onto the primary amino groups, Chitosan-4-thio-butyl amidin-conjugates (chitosan TBA), Hyaluronic acid and derivatives, Pectin and traganth, Starch, Sulfated polysaccharides such as heparin, dextran sulfate, sulfated cyclodextrins, Carrageenan, Gelatin, Sodium carboxy methyl cellulose (CMC) and derivatives, methyl cellulose (MC), Synthetic polymers such as poly(acrylic acid) (PAA) and derivatives, hydroxypropyl methylcellulose and poly(methylacrylate) derivatives, and thiolated polymers.

In one preferred embodiment of the invention, the mucoadhesive backbone is a polymer, most preferably alginate. Thus, there are provided the following compounds of the general formula $A-(B)_n$, wherein A is alginate, B is an antibody and n is 1, 2, 3, 4, 5, 6, 7, 8, 9 or 10. In one preferred embodiment, B is an antibody capable of binding to a virus selected from adenovirus, rhinovirus, Rift Valley virus, Ebola virus, and influenza virus.

There are thus provided the following conjugates:

A conjugate of alginate with an antibody for an adenovirus,

A conjugate of alginate with an antibody for a rhinovirus,

A conjugate of alginate with an antibody for the Rift Valley virus,

A conjugate of alginate with an antibody for the Ebola virus,

A conjugate of alginate with an antibody for an influenza virus.

Preferably, the ratio of alginate to the antibody is 1 to 1, 1 to 2, or 1 to 3, respectively. The ratio of alginate to the antibody may also be 1 alginate to at least 4 antibodies.

The compound of the general formula $A-(B)_n$, also termed the "mucoadhesive ligand" may be one having a mucoadhesive backbone with at least one ligand group, B, emerging therefrom in an arrangement which may be symmetric or asymmetric and may comprise a single type ligand, i.e. being selective towards a single toxin, or a multi-type ligand, i.e. being selective to a range of toxins. Non-limiting arrangements of the compounds of general formula $A-(B)_n$ are shown in FIGS. 1A-E.

The "ligand group", B, refer to an ion, a functional group or a side group, which is chemically substituted (namely, having at least one bond therewith, such bond may be covalent, ionic, electrostatic, hydrogen bond, van der Waals interaction, London force or any combination thereof) onto the mucoadhesive backbone, A, or embedded therein by means of physical attraction and which is capable of interacting with a toxin to which it is exposed. This interaction, e.g. by formation of a bond (namely, having at least one bond therewith, such bond may be covalent, ionic, electrostatic, hydrogen bond, van der Waals interaction, London force or any combination thereof) may be such that allows strong enough interaction with said toxin so as not to allow release of the toxin, once captured, back into the mucosal membrane. Such interaction may through any type of chemical or physical interaction and, for example, may be through co-ordinate covalent bond and may be polydentate or bidentate in nature.

The ligand group may also be a reactive group that undergoes a chemical transformation when in contact with the toxin. For example, the ligand may be an unsaturated carbon chain capable of undergoing reduction e.g., halogenation in exposure to toxins (e.g. halogens) or may be a metal ion capable of undergoing a redox-type transformation upon exposure to a variety of chemical toxins. The ligand may also be a liposome or a micro- or nanoparticle capable of enclosing a toxin.

The ligand group may also be a so-called proligand which is susceptible to chemical transformation in the targeted organ, thereby transforming into a reactive entity only when arriving at the target membrane. For example, a proligand may be an esterified acidic chain which undergoes acidic saponification at the target membrane, reverting into the active acidic chain and binding the toxins which it encounters.

The ligand functional group may for example be a unsaturated carbon chain of at least two carbon atoms, aromatic rings, crown ethers, cryptates, amides, carboxylic acids, esters, sulfonates, sulfoxides, sulfoneamides, porphyrins, metalloporphyrins, bis(dimethylglyoximate), bis(acetylacetonato), bis(8-quinolinato), bis(4-fluorosalicylaldeydato), N,N'-ethylenebis salicylideneiminato and the like. The ligand may also be a macromolecule or a biologically active molecule such as a soluble receptor or a receptor antagonist, protein or an antibody which is capable of interacting with a toxin such as a virus.

In one preferred embodiment, B is an antibody capable of interacting with a virus (the toxin) selected from Variola major and other pox viruses; Arenaviruses such as Junin virus, Machupo virus, Guanarito virus, ymphocytic choriomeningitis virus, Lassa virus; Bunyaviruses such as Hantaviruses, Rift Valley fever virus; Flaviruses such as Dengue fever viruses; Filoviruses such as Ebola virus, Marburg virus; Eastern equine encephalitis virus, Western equine encephalitis virus, Venezuelan equine encephalitis virus, La Crosse virus, Japanese encephalitis virus, Kyasanur forest virus, California encephalitis viruses; food and waterborne Pathogens such as Caliciviruses; Hepatitis A virus; Nipah virus; Yellow fever virus; Influenza viruses; Rabies virus and other Hantaviruses.

In another embodiment, the ligand group B is a ligand capable of trapping pollen particles, chemically, i.e. by binding to one or more components which cover the outer surface of the pollen, or physically, i.e. by engulfing the pollen. Such ligand groups may be selected from amino acids such as phenylalanine, leucin, valine, isoleucine, arginine, histidine, lysine, methionine and others which may be bonded to the polymer A through the C- or N-terminal of the amino acid group; short peptides not exceeding about 10 kD in size, which may be connected to the polymer A through the C- or N-terminal; sugars such as fructose, glucose or sucrose which may be connected to the polymer A through one or more of the alcohol groups or oligo or polysaccharides. Physical trapping of the pollen may take place, as will be shown below, for example, by the mucoadhesive polymer itself which interacts with the pollen by engulfing it.

The mucoadhesive backbone and the ligand as a whole may be obtained from mammalian tissues, such as hyaluronic acid, dermatan sulfate and chondroitin sulfate; from the exoskeleton of crustaceans, such as chitin that further deacetylated to obtain chitosan; from vegetables and plants, such as starch and starch derivatives; from aquaculture sources such as alginate, or they may be synthetically modified in order to obtain the desired ligand-toxin specificity or interaction.

The term "toxin" as used herein refers to a substance which can cause a long-term or short-term, local or systemic toxicity to the mucosal membrane, the organ said membrane is associated therewith or to the whole animal body (human or non-human). Such toxicity may for example be an allergic reaction or any other long-term or short-term non-allergic reaction such as viral infection, bacterial infection, fungal infection, poisoning by biotoxins and others.

The toxins may enter the body of the subject through the opening of a body cavity, e.g. mouth, nose by inhalation or by contamination by other airborne particulates or by other particulate contaminants. The origin of the toxins may also be the body itself. For example, toxins which are expelled from the body through breathing may be captured by the mucoadhesive compounds, thereby minimizing exposure of the subject's environment to said toxins.

Examples of particulate toxins, without being limited thereto are pollen, dander, mold, spores of various origins and dust. Examples of chemical toxins are gas, vapor or dust molecules from industrial, medicinal or other environmental sources such as halogen gases, e.g., bromine, chlorine gases, chlorofluorocarbon (CFCs), NOx, SOx, CO, nicotine, nicotine by-products, smoking by-products such as acetaldehyde, formaldehyde and others, metal ions, charged or uncharged molecules such as silicon, asbestos, chemical warfare agents, and others. Also included are biological toxins (biotoxins) such as animal or plant toxins, viruses, bacteria, fungus, and biological warfare agents.

Non-limiting examples of the viral toxins are Adenoviruses, Arboviruses, Arenaviruses, Encephalitis, Orthomyxoviruses, Papillomaviruses, Paramyxoviruses, Picornaviruses, Poxviruses, Retroviruses, Rhabdovirus, and Rhinoviruses. Specific examples are Variola major and other pox viruses; Arenaviruses such as Junin virus, Machupo virus, Guanarito virus, ymphocytic choriomeningitis virus, Lassa virus; Bunyaviruses such as Hantaviruses, Rift Valley fever virus; Flaviruses such as Dengue fever viruses; Filoviruses such as Ebola virus, Marburg virus; Viral encephalitis such as West Nile virus, Eastern equine encephalitis virus, Western equine encephalitis virus, Venezuelan equine encephalitis virus, La Crosse virus, Japanese encephalitis virus, Kyasanur forest virus, California encephalitis viruses; Food and Waterborne Pathogens such as Caliciviruses; Hepatitis A virus; Nipah virus; Tickborne hemorrhagic fever viruses such as Crimean-Congo hemorrhagic fever virus; Tickborne encephalitis viruses; Yellow fever virus; Influenza and avian influenza viruses; Rhinoviruses, Rabies virus and other Hantaviruses.

Non-limiting examples of the bacterial toxins are *Bacillus anthracis; Clostridium botulinum; Francisella tularensis; Yersinia pestis; Burkholderia pseudomallei; Burkholderia mallei; Clostridium perfringens; Coxiella burnetii; Brucella melitensis, abortus, suis,* and *canis; Staphylococcus aureus; Rickettsia prowazekii; Chlamydia psittaci*; Food and Waterborne Pathogens such as *Escherichia coli* O157:H7, *Vibrio cholerae, Salmonella species, Shigella* species, *Listeria monocytogenes, Campylobacter jejuni, Yersinia enterocolitica; Mycobacterium tuberculosis*; and other *Rickettsia*.

Non-limiting examples of chemical warfare agents are the persistent or non-persistent nerve agents such as tabun, sarin, soman, GF, and VX (methylphosphonothioic acid); blister agents such as sulfur mustard, nitrogen mustard, Lewisite, and phosgene oximine; choking agents such as phosgene, diphosgene, chlorine and chloropicrin. Also included are lacrimators such as chlorobenzylidenemalononitrile, chloroacetophenone, and nitrochloromethane.

Non-limiting examples of the biological warfare agents are anthrax, Botulinum toxins, Brucellosis, cholera, *Clostridium perfringens* toxins, Congo-Crimean hemorrhagic toxins, Ebola, Melioidosis, plague, Q fever, ricin, Rift valley toxin, Saxitoxin, smallpox, Staphylococcal enterotoxin B, Trichothecene mycotoxins, tularemia, and Venezuelan equine encephalitis.

Other toxins may be food and waterborne pathogens such as *Cryptosporidium parvum, Cyclospora cayatanensis, Giardia lamblia, Entamoeba histolytica, Toxoplasma gondii, Microsporidia*, and plant pathogens such as *Ricinus communis* Castor bean.

Preferably, the toxins are pollen, dander, mold, and dust, variola major, Marburg toxin, Rift Valley fever virus, Ebola virus, *Clostridium botulinum* toxin, Anthrax *Bacillus anthracis*, RSV, Rhinoviruses, spores of *Aspergillus* sp., yeast of *Cryptococcus neoformans*, arthro spores such as *Coccidiodes immitis* and Influenza.

Also encompassed are toxins which are unique to hospitals which are capable of causing the so-called hospital associated infections (HAI). One example of such a toxin is the methicillin-resistant *Staphylococcus aureus* (MRSA). MRSA is the most infamous hospital pathogen, with levels of resistance increasing from 3% in 1992 to 43% in 2002 in England and Wales (HPA 2003). However, HAI caused by other microorganisms such as vancomycin-resistant enterococci (VRE), *Clostridium difficile, Acinetobacter baumannii* and multidrug resistant (MDR) *Acinetobacter* sp. are becoming increasingly prevalent and are thus within the scope of the term toxin.

The presence of or contact with such toxins may directly or indirectly result in the occurrence of local or systemic disorders or diseases which are known to be associated with the specific toxin (pathogen) or the family with which it is associated. Such diseases or disorders may be diseases of the respiratory system, e.g. asthma, adult and infant respiratory distress syndrome, suffocation, atelectasis, bronchiectasis, carbon monoxide poisoning, cancer, chronic obstructive pulmonary disease, cystic fibrosis, fluid accumulation in the alveoli, pneumonia, sinusitis, tuberculosis, and others; viral infections, e.g. Smallpox, Argentine hemorrhagic fever, Bolivian hemorrhagic fever, Venezuelan hemorrhagic fever, Lymphocytic choriomeningitis, Lassa fever, Hantavirus pulmonary syndrome, Rift Valley fever, Dengue fever, Ebola hemorrhagic fever, Marburg hemorrhagic fever, Eastern equine encephalitis, Western equine encephalitis, Venezuelan equine encephalitis, La Crosse encephalitis, Japanese encephalitis, Kyasanur forest disease, California encephalitis, Gastroenteritis, Hepatitis A, Nipah virus encephalitis, Crimean-Congo hemorrhagic fever, Yellow fever, Flu, Rabies, and others; bacterial infections, e.g. Anthrax, Botulism, Tularemia, Plague, Melioidosis, Glanders, Epsilon toxin, Q fever, Brucellosis/Undulant fever, Enterotoxin B, Epidemic typhus, Psittacosis, Diarrheagenic *E. coli*, Cholera, venereal disease, Salmonellosis, Shigellosis, Listeriosis, Campylobacteriosis, Yersiniosis, Multidrug-resistant Tuberculosis, and Rickettsial diseases; and diseases and disorders associated with food and waterborne toxins such as Cryptosporidiosis, Cyclosporiasis, Giardiasis, Amebiasis, Toxoplasmosis, Microsporidiosis, and others.

In a further feature of the present aspect, there is provided a further mucoadhesive ligand having the formula $(D)_m$-A-$(C)_n$, wherein A is a mucoadhesive polymer, C is a first ligand group being chemically substituted to A and capable of interacting with a toxin, D is a second ligand group being chemically substituted to A and reversibly chelated to an agent capable of being released from said second ligand group, n and m each independently integers greater than 1. Non-limiting examples of the compounds of general formula $(D)_m$-A-$(C)_n$ are shown in FIGS. 2A-C.

Upon application of a compound of the general formula $(D)_m$-A-$(C)_n$, or a composition comprising thereof, to the mucosal membrane, the second ligand group, D, may release its chelated agent to the mucosal membrane or to the environment thereof, and the free ligand group, C, may act to remove therefrom any toxin for which it is designed.

The compound of the general formula $(D)_m$-A-$(C)_n$, may be administered in a fully loaded form, namely having a substantial number of said D groups bound to an agent to be released into the mucosal membrane. Preferably, the compound of the general formula $(D)_m$-A-$(C)_n$, is used with a maximal number of said ligands, D, being bound to an agent to be released.

The compound of the general formula $(D)_m$-A-$(C)_n$, may also be administered in a partially-bound form, namely having only a portion of said D groups bound to an agent to be released into the mucosal membrane. The term "partially" or "semi" does not stand to mean any specific number or percentage of bound or loaded ligands from the total number of ligand groups attached to the backbone of any one mucoadhesive backbone. The following non-limiting exemplary ligands are considered as semi-loaded ligands: a) a polymer A having 100 ligand groups D of which one is loaded; b) a polymer A having 2 ligand groups D of which one is loaded; c) a polymer having 50 ligand groups D of which 48 are loaded, etc.

Such partially-loaded mucoadhesive ligands may be used in the method disclosed herein for removal of toxins from mucosal membranes and have the added benefit of being able to replenish or deliver selected substances to the membrane or environment from which toxins are to be removed. Examples of substances which may be delivered to the membrane are: metal ions such as sodium, magnesium, calcium; sugars, drugs; enzymes; growth-stimulating agents; antidepressant agents; antibiotics; antiviral agents; antiprotozoal agents; vitamins; and other agents which typically form part of the mucosal membrane.

In one specific embodiment, the release of the substance from the loaded ligand may be simultaneous with the capture of the toxin by the free ligand C or may be independent thereof. In another specific embodiment, said release is dependent on binding by the free ligand group C by a toxin.

The ligand groups designated herein by B, C and D may be arranged on the polymer A backbone randomly or selectively as decided by the person synthesizing the compounds of the invention. Exemplary, non-limiting arrangements are shown in FIGS. 1A, B, C, D, E and 2A, B and C. In these figures, A and B are as defined hereinabove. The entities labeled L are the chelation cavity or active site of the ligand groups B to which the toxin attaches.

All compounds of the present invention may be biodegradable, non-biodegradable or partially biodegradable in nature and may be selected based on several parameters such as their intended use and targeted mucosal membrane.

The compounds of the invention may be used for the preparation of a therapeutic, prophylactic or hygienic compositions, for example for the prevention of a disease or disorder associated with the exposure to an opportunistic toxin entering the environment surrounding said membrane and which contact with said membrane may bring about a direct or indirect toxicity (such as allergies, poisoning, infections etc). In one embodiment, said compounds are used for the preparation of a composition suitable for therapeutic purposes such as to prevent or reduce the concentration of a certain toxin in a mucosal membrane. In another case, the compositions are used for hygienic purposes.

In a further embodiment, the compositions of the present invention may further comprise one or more of a variety of agents such as for example pH adjusters, carriers, excipients, diluents, antibiotics, antioxidants, vehicles such as starch, microcrystalline cellulose, lactose, sorbitol, or mannitol; lubricants such as magnesium stearate, glycerol behenate, talc, hydrogenated ricin oil or waxes; flow agents such as colloidal silica; aromas, flavouring agents, sugaring or sweetening agents and in general any substances capable of improving taste, odor or appearance of the composition, and one or more pharmaceutical agents such as glucocorticoids, dexamethasone, dexamethasone salts, isothiozolones, anticoagulants, heparin, hirudin, peptides such as oligopeptides and polypeptides, oligopeptides, antimitotic agents, angiopeptin, polynucleotides, and oligonucleotides, sulfyhdryls, hydroxamic acids, oral compositions including bioadhesive syrups and gels, mouth wash, cough syrups and oral gels for mouth sores.

The composition to be administered are typically administered directly, namely in case of the respiratory system and the GI tract—intranasally or per oral as a liquid or sprayed into the oral cavity or on the back of the throat; in case of the vagina as suppositories, vaginal rings, tablets, capsules, powders, granules, or microgranules. The composition may also be delivered topically, for example, to the oral cavity or to the vagina as a dry powder which encores to the mucosal membrane after having absorbed water therefrom or after having been absorbed therein. The frequency of application may vary considerably, for example from once per day to several times per day, or once or more in several days, depending for example on the condition of the subject in need of such composition. The composition may also be administered by any other regimen as known to a person skilled in the art.

In another embodiment of the present invention, the composition comprising of the mucoadhesive ligand may further comprise or be administered in conjunction with enzyme inhibiting agents such as reverse transcriptase inhibitors, protease inhibitors, angiotensin converting enzymes, 5-alpha-reductase, and the like. Typical agents include peptide and non-peptide agents including finasteride, lisinopril, saquinavir, quinapril, ramipril, indinavir, ritonavir, nelfinavir, zalcitabine, zidovudine, allophenylnorstatine, kynostatin, delaviridine, bis-tetrahydrofuran ligands, and didanosine.

The pharmaceutical composition of the present invention may be formulated in the form of suppositories, tablets, films, patches, and gels for oral, buccal, nasal, ocular, and vaginal routes; as well as spray formulations, drops, dry powder, suspensions and the like. The composition may additionally be formulated as microparticles or nanoparticles.

In another aspect of the present invention, there is provided a method for toxin removal from a mucosal membrane or the environment thereof, said method comprising contacting said mucosal membrane with an effective amount of a composition comprising at least one compound of the general formula A-$(B)_n$, as defined herein.

In one embodiment, the mucosal membrane is ex-vivo, namely it is not part of a living animal body but rather one which is used for example for laboratory, research or other medicinal applications. Such membrane may be in a laboratory apparatus or a Petri dish or in any other form as may be appropriate. In another embodiment, said mucosal membrane is in a living animal such as human or non-human animals. Preferably, it is part of a human.

The invention further provides a method for the prevention of a disease or disorder of the mucosal membrane, said disease or disorder being associated with a toxin, said method comprising contacting a mucosal membrane of a subject with an effective amount of a composition comprising at least one compound of the general formula A-$(B)_n$.

The invention still further provides a method for the prevention of a disease or disorder, comprising contacting a mucosal membrane of a subject with an effective amount of a composition comprising at least one compound of the general formula A-$(B)_n$.

The invention in yet another of its aspects provides a method for shielding a mucosal membrane from contacting toxins or being penetrated thereby or adsorbed thereto, comprising contacting said mucosal membrane with an effective amount of a composition comprising at least one compound of the general formula A-(B)$_n$.

Preferably, the mucosal membrane is selected from a membrane of the upper or lower respiratory system, more preferably to the mouth, gastrointestinal tract (GI tract), nose, nasal cavity, larynx, trachea, pharynx, vagina, rectum or urethra. In some embodiments, more than one membrane may be treated at one time, with an identical or different composition. In one example, both the nasal and GI tract are treated with a composition comprising a conjugate of alginate and an antibody for the Rift Valley virus. In another example, the nasal mucosa is treated with a conjugate of alginate and an antibody for the Rift Valley virus and the vagina is treated with a different conjugate or a composition comprising same.

Most preferably, the mucosal membrane is related to the respiratory system and specifically to the upper respiratory system.

The administration of the compositions of the invention may be by any known method as disclosed herein. Preferably, the compositions are administered directly to the mucosal membrane by topical administration or by direct contact therewith.

The term "contacting" as used herein is synonymous to "administration". The terms or any lingual variation thereof refer typically to topical administration of the composition of the invention directly to the mucosal membrane, utilizing any type of application known to a person skilled in the art. The composition to be administered is typically applied directly by touching the membrane with the composition. For example, in the case of the respiratory system and the GI tract, the composition may be administered intranasally or per oral as a liquid or sprayed into the oral cavity or on the back of the throat. In case of the vagina, the composition may be administered as suppositories, vaginal rings, tablets, capsules, powders, granules, or microgranules. The composition may be delivered topically with the frequency of application ranging from once per day to several times per day, or once or more in several days, depending on the condition of the subject in need of such composition. The composition may also be administered by any other regimen e.g. systemic administration. The composition of the invention may be administered in a dosage form or in separate dosages.

The invention further provides the use of mucoadhesive polymers such as alginate for the preparation of a composition for toxin removal from a mucosal membrane or its environment, such as the skin surrounding the body cavity. The mucosal membrane composition which is administered to the surrounding of the mucosa may be applied in any known method, e.g. as a skin ointment.

Mucoadhesive polymers which are capable of entrapping a toxin as defined herein may be used also for the treatment of disease and disorders of the mucosal membrane or disease and disorders which are associated with the penetration of such toxins through the mucosal membranes.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1A:
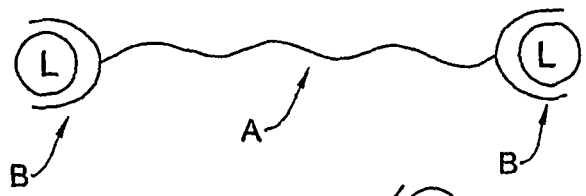
FIGS. 1A-E are schematic representations of various exemplary mucoadhesive ligands (A=mucoadhesive backbone; B=ligand or chelating group; and L=chelation cavity).
Figure 1B:
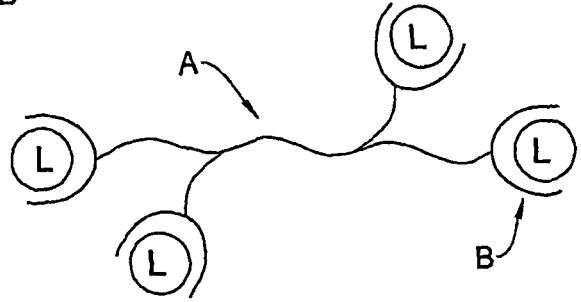
Figure 1C:
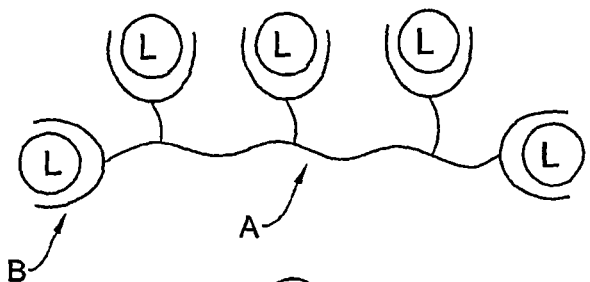
Figure 1D:
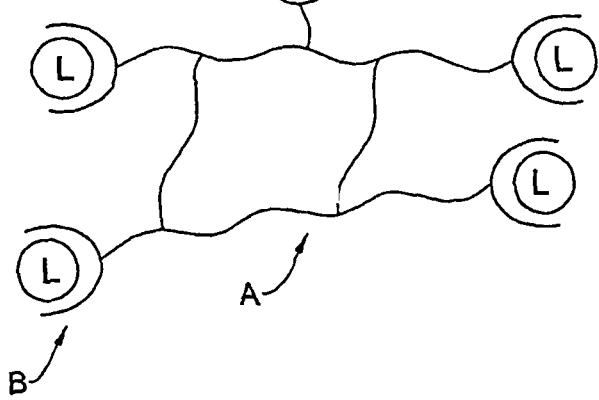
Figure 1E:
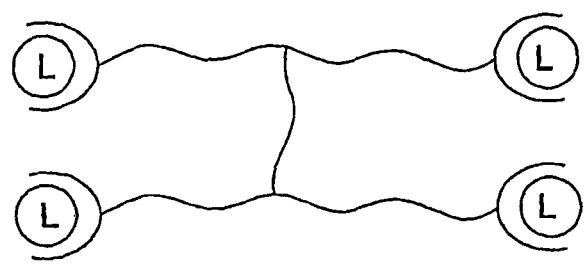

The mucosal membrane may be in the mouth, gastrointestinal tract (GI tract), nose, nasal cavity, larynx, trachea, pharynx, vagina, rectum or urethra and may absorb or be in direct contact with toxins which penetrate it or reside in its environment such as the volume of air above it or in the liquid which surrounds it. The ligands of the present invention are capable of bonding irreversibly (or substantially irreversibly for the period of their residence in the subject's body) to such toxins and assist in their removal from the treatable environment, e.g. the respiratory system. Removal of such toxins from the treated environment may allow in the prevention of conditions such as those disclosed hereinbelow or in the treatment of an existing condition by reducing the concentration of a toxin in the treated organ, i.e. the respiratory system, nasal cavity, vagina and the like.

The term "respiratory system" refers to the complete respiratory system, but preferably relates to the upper respiratory system which includes the nasal cavity, the pharynx, trachea and larynx.

The nasal cavity is divided laterally into two mucus-coated passages, one from each nostril, by a midline septum containing hyaline cartilage. From both lateral walls of the septum into the two cavities are extending three curved plates of bone, the superior, middle, and inferior conchae (turbinate bones) which are covered by mucous membrane. The inferior and middle conchae are covered by respiratory epithelium and the superior concha is covered by olfactory epithelium. The conchae function by increasing the surface area containing respiratory epithelium and by creating turbulence thus resulting in increase contact of the air and the airborne toxins with the epithelium allowing the mucus secreted by the respiratory epithelium to trap these toxins and allowing humidification and warming of the air.

The pharynx connects the nasal and oral cavities to the larynx and esophagus and acts as a passageway for air and food. The parts of the pharynx with food contact (oropharynx and laryngeal pharynx) are lined by nonkeratinizing-stratified squamous epithelium. The part of the pharynx above the soft palate, the nasopharynx, is lined by pseudo-stratified ciliated columnar epithelium with goblet cells. The connective tissue of the pharynx is fibroelastic surrounded by striated muscle of the pharyngeal muscles. The pharyngeal tonsil, located in the midline of the posterior wall of the nasopharynx, is made up of multiple confluent lymphoid nodules intimately associated with the pseudo-stratified columnar epithelium.

The larynx contains hyaline and elastic cartilage forming a complex muscular (skeletal) architecture that maintains passage, prevents swallowed food or liquid from entering the trachea in a valve-like manner, and controllably produces sound. The epiglottis with its central elastic cartilage plate extends into the pharynx has stratified squamous epithelium on its anterior portion (continuous with posterior surface of tongue). The posterior surface has a ciliated, pseudo-stratified columnar epithelium containing seromucous glands. The mucosa below the epiglottis has two pairs of folds forming the vocal cords. The upper pair represents the false (ventricular) vocal cords typically covered by respiratory epithelium with serous glands within the lamina propria. The lower pair constitutes the true vocal cords that are covered by a stratified squamous epithelium devoid of glands.

Trachea morphology is best characterized by the large C-shaped rings of hyaline cartilage, like 16-20 stacked horseshoes, which maintain patency of this passageway to the lungs. This flexible, semi-rigid tubular structure terminates where it bifurcates into the two main bronchi. The posterior open portion of the cartilage rings is bridged by fibroelastic ligament and smooth (trachealis) muscle. Contraction of this muscle permits some constriction of the tracheal lumen whereas the ligament prevents dilation by overdistension. The luminal surface is typical respiratory epithelium, containing columnar ciliated cells, mucus secreting goblet cells, undifferentiated (stem) basal cells, and submucosal seromucous glands.

The term "mucoadhesive" as used herein refers to a phenomenon where a substance (of any source, i.e., natural, synthetic or a combination thereof), when applied to a mucosal epithelium, adheres to the mucosal layer for a period of time sufficient to bind to airborne or other toxins, as discussed herein. The mucoadhesive substances, which are typically polymers, may be natural or synthetic and may be neutral or charged (anionic or cationic).

Such substances adhering to the mucosal layer may have varying retentive qualities. The preferred mucoadhesive substances are those that are additionally "mucoretentive". The retentive properties of such substances refer to the substance's, or composition containing thereof, degree of resistance to washing and dissolving forces of fluids in the respiratory system.

The mucoadhesive properties of the substances used and their capability in binding and removing toxins which approach the mucosal membrane may be assessed by comparison to control compositions that do not contain the mucoadhesive substance.

Generally speaking, the compounds of the invention are bifunctional, namely have: (1) a polymer as the mucoadhesive backbone, which promotes adhesiveness and retention of the mucoadhesive ligand to the mucus membrane, and (2) at least one functional group, a ligand or a chelator, which is capable of bonding, chemically or physically with the toxin or a ligand or chelator already loaded with a certain agent which may be released after application to the mucus membrane for example for replenishment of said agent.

Also encompassed within the scope of the invention are those ligand molecules which although lacking a distinctive backbone, still maintain mucoadhesiveness and chelator properties. Such may for example be liposomes.

Figure 10:
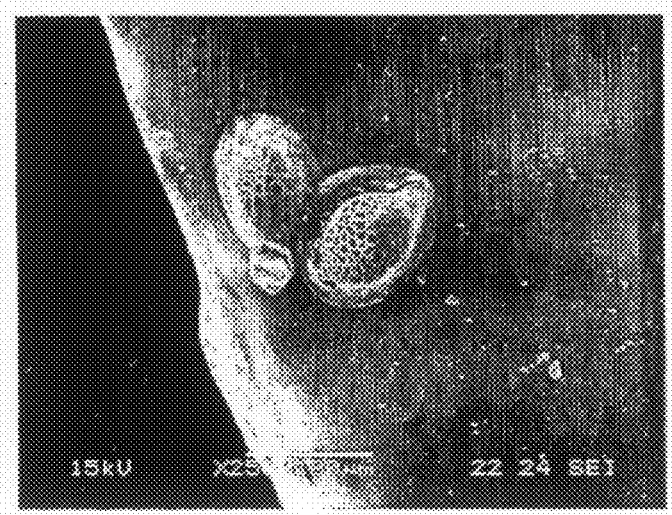
FIG. 10 shows a scanning electron microscope (SEM) picture of free (unsubstituted) alginate entrapping Easter Lily pollen.

Binding of the toxin may also be achieved through the mucoadhesive backbone and not via the chelating functional group. In such cases, in the general formula A-(B)$_n$ the mucoadhesive substance itself may act as the ligand system and the ligand group may need not be present (n=0). Such a binding power is shown in the SEM picture of FIG. 10, which depicts free alginate after having contacted a concentration of Easter lily pollen. The entrapment of the pollen within the polymer is exhibited.

Additionally, the mucoadhesive ligands may be constructed as a nanoparticles or microspheres. Suitable mucoadhesive microspheres are for example carboxyvinyl mucoadhesive microspheres, chitosan microspheres, Eudragit floating microspheres, and cholestyramine microparticles.

The ligand groups may be such groups that are part of the mucoadhesive backbone or may be selectively attached thereto using chemical transformations as known to a person skilled in the art of organic or inorganic synthesis (see for example: Organic Synthesis, John Wiley & Sons, New-Jersey, 2003; Sandler S R., Karo W., Organic Functional Group Transformations, Academic Press, 1971; Fieser and Fieser, Reagents for Organic Synthesis, John Wiley & Sons, 1967; Protective Groups in Organic Chemistry, McOmie J F W., Ed. Plenum Press, 1973; Chemical Reactions of Polymers, Fettes E M., Ed. Intersience Publishers, New-York; Koenig J L., Spectroscopy of Polymers, $2^{nd}$ Ed. Elsevier, 1999). The preferred mucoadhesive backbone is a polymer or a polysaccharide.

The useful method of site-directed conjugation of antibody molecules takes advantage of the carbohydrate chains attached to the $C_H^2$ domain within the Fc region. Mild oxidation of the polysaccharide sugar residues with sodium periodate will generate aldehyde groups. A cross-linking or modification reagent containing a hydrazide functional group then can be used to target these formyl groups specifically for coupling to another molecule (alginate backbone). Directed conjugation through antibody carbohydrate chains thus avoids the antigen binding regions while allowing for use of intact antibody molecules. This method often results in the highest retention of antigen binding activity within the ensuing conjugate.

As used herein, the term "antibody" is intended to include immunoglobulin molecules and immunologically active portions of immunoglobulin molecules, i.e., molecules that contain an antigen binding site that specifically binds an antigen (or a toxin), such as Fab and F(ab')$_2$ fragments. As used herein, the term includes polyclonal and monoclonal antibodies, and variants such as single-chain (recombinant) antibodies, "humanized" chimeric antibodies, and immunologically active fragments of antibodies. For the purposes of this invention, a "chimeric" monoclonal antibody is a murine monoclonal antibody comprising constant region fragments (Fc) from a different animal. For the purposes of this invention, a "humanized" monoclonal antibody is a murine monoclonal antibody in which human protein sequences have been substituted for all the murine protein sequences except for the murine complementarity determining regions (CDR) of both the light and heavy chains. Standard techniques for the generation and isolation of antibodies are well-known and commonly employed by those of skill in the art. A number of standard techniques are described in Kohler Milstein, Nature 256:495-97 (1975); Kozbor et al., Immunol Today 4:72

(1983); Cole et al., Monoclonal Antibodies and Cancer Therapy, pp. 77-96 (Alan R. Liss, Inc., 1985); Kenneth, in Monoclonal Antibodies: A New Dimension In Biological Analyses (Plenum Publishing Corp., New York, N.Y. 1980); Lerner, Yale J. Biol. Med., 54:387-402 (1981); Gefter et al., Somatic Cell Genet., 3:231-36 (1977); and Galfre et al., Nature 266:55052 (1977).

As stated above, each mucoadhesive polymer can carry one or more biologically active ligands linked to the polymer by a prodrug linker or any other linker known to the person skilled in the art. The polymers may have further substituents and may be further functionalized. Non-limiting examples of such functional groups comprise carboxylic acid and activated derivatives, amino, maleimide, thiol, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl, arylating agents like aryl fluorides, hydroxylamine, disulfides like pyridyl disulfide, vinyl sulfone, vinyl ketone, diazoalkanes, diazoacetyl compounds, epoxide, oxirane, and aziridine.

The averaged molecular weight of an antibody is on the order of 150,000 Da while the averaged molecular weight of a monomer unit of a polymer such as sodium alginate is 198 Da. Such a large difference in molecular weights and size, along with a large variety in structural conformations associated with the macromolecule, e.g. the antibody, may result in steric hindrances which will allow relatively low degree of molar modification. Assuming the polymers to be monodispersed with an average molecular weight of Mw=150,000 Da, and without wishing to be bound by theory, it is believed that an efficient mucoadhesive ligand would be one having between 1 and 3 antibody molecules per each single polymer chain molecule, or in other words, a single macromolecule for every 750 monomer unites of the polymer (150,000 Da/198 Da=750 monomer units). Assuming a ration of 3 macromolecules per polymer, the percent coverage may be at least 0.4%. Using high molecular weight polymer, being of, for example, 1,000.000 Da in size allows a greater macromolecule converge in the order of between 2 and 10%.

In case of low molecular weight ligands, comparable with alginate monomer molecular weight the percent coverage is about 50% of total functional group coupled.

Preferred functional groups for the polymer include but are not limited to thiol, maleimide, amino, carboxylic acid and derivatives, carbonate and derivatives, carbamate and derivatives, aldehyde, and haloacetyl. Especially preferred functional groups include thiol, maleimide, amino, carboxylic acid and derivatives, carbamate and derivatives, and carbonate and derivatives thereof.

The viscoelasticity of mucoadhesive backbone has a great effect on its adhesiveness and cohesiveness. By adsorbing, swelling and capillary action, the mucoadhesive backbone takes up water from the mucus membrane, which leads to a strong adhesion. The evaluation of a certain substance as potentially capable of strong adhesiveness and long-mucus retention may be determined in accordance with numerous tests known to a person skilled in the art. The simplest test for adhesiveness is the tensiometry experiment which measures the force required to detach two surfaces (Biochemical Society Transactions, vol. 31, part 5, 1036-1040, 2003). The mucoadhesive property of the mucoadhesive ligands may also be evaluated by an in vitro adhesion testing method known as the wash-off method. The mucoadhesiveness of these ligand molecules may be compared with that of a non-mucoadhesive material, such as ethylene vinyl acetate.

The term "effective amount" as used herein refers generally to the amount which is effective to remove from the mucosal membrane a maximum amount of absorbed or adsorbed toxin which may be sufficient to prevent adsorption or absorption of the a toxin making contact with the membrane, ex vivo or in vivo, or to prevent or delay the onset of a disease or disorder associated with said toxin. The term "preventing" or any lingual variation thereof, refers to precluding a disease or disorder which is associated with an exposure to said toxin from occurring, or reducing symptoms associated with an existing disease or disorder, or inducing a pharmacological change or hygienic result relevant to treating the disease or disorder, or minimizing complications and side effects of a disease or disorder or the occurrence of a secondary disease or disorder which may result therefrom, or arresting or delaying the onset of clinical changes associated with such a disease or disorder. The appropriate dosage for the pharmaceutical agents will often be approximately comparable to that of the mucoadhesive ligand alone; dosages may vary considering many factors including age, weight, and condition of the subject needing such composition, as well as the pharmacokinetics of the specific agent. The composition of the invention may contain one or more mucoadhesive ligand; however, their proportion in the composition will typically be sufficient to procure the required therapeutic or hygienic action.

In another aspect of the present invention there are provided pharmaceutical compositions comprising any one of the mucoadhesive ligands utilized with the method of present invention. Also contemplated by the present invention are various uses for such mucoadhesive ligands, i.e. as therapeutics and for hygiene.

The compositions of the present invention may further comprise one or more of a variety of agents such as for example pH adjusters, carriers, excipients, diluents, antibiotics, antioxidants, vehicles such as starch, microcrystalline cellulose, lactose, sorbitol, or mannitol; lubricants such as magnesium stearate, glycerol behenate, talc, hydrogenated ricin oil or waxes; flow agents such as colloidal silica; aromas, flavoring agents, sugaring or sweetening agents and in general any substances capable of improving taste, odor or appearance of the composition, and one or more pharmaceutical agents such as glucocorticoids, dexamethasone, dexamethasone salts, isothiozolones, anticoagulants, heparin, hirudin, peptides such as oligopeptides and polpeptides, oligopeptides, antimitotic agents, angiopeptin, polynucleotides, and oligonucleotides, sulfyhdryls, hydroxamic acids, oral compositions including bioadhesive syrups and gels, mouth wash, cough syrups and oral gels for mouth sores.

These agents may be hydrophobic, hydrophilic or amphiphilic in nature and can belong to a specific therapeutic class or within an area covering cardiovascular, bronchodilation, enzyme supplements, estrogen and androgen supplements, growth-stimulating supplements, anti-parkinsonism, memory maintenance, memory retention or enhancement, anti-anxiety, antidepressant, birth-control, antibiotic, antiviral, antiprotozoal, vitamin, antidiabetic, gastrointestinal, anti-convulsant, immunomodulation, nutritional supplements and appetite modulating therapy.

These agents may be part of the composition itself or alternatively may be synthetically attached to the mucoadhesive ligand. For example, in one case the polymer mucoadhesive ligand may have an appetite-modulating agent attached thereto. When applied to the mucosal membrane, the polymeric backbone releases said agent without affecting its ability to attach to toxin molecules present in the membrane.

Suitable pH adjusting substances include any such substance that is safe for mammalian use. More preferably, the pH adjusting substances include any weak acid or weak base, e.g., sodium carbonate, potassium carbonate, disodium hydrogen phosphate, sodium dihydrogen phosphate, and the equivalent potassium salts.

Examples of peptides are, without being limited thereto, cytokines, proteins, enzymes, hormones, monoclonal antibodies, human growth hormones, clotting factors, colony stimulating factors, erythropoietins, tissue plasminogen activators, recombinant soluble receptors, anti-bacterial agents, anti-neoplastic agents, anti-fungal agents, immunomodulators, antiparasitic agents, CNS agents and vaccines.

Examples of polypeptides, without being limited thereto, are antibodies, immunomodulators or cytokines, e.g. interferons or interleukins, peptide hormones, e.g. colony stimulating factors and tumor necrosis factors, hormone receptors, neuropeptides, lipoproteins, erythropoietins, growth hormones, thyroid hormones, toxins such as diphtheria toxin, proteoglycans such as hyaluronic acid, and glycoproteins such as gonadotropin hormone.

The pharmaceutical composition comprising of the mucoadhesive ligand may be administered also in conjunction with enzyme inhibiting agents such as reverse transcriptase inhibitors, protease inhibitors, angiotensin converting enzymes, 5-alpha-reductase, and the like. Typical agents include peptide and nonpeptide agents including finasteride, lisinopril, saquinavir, quinapril, ramipril, indinavir, ritonavir, nelfinavir, zalcitabine, zidovudine, allophenyinorstatine, kynostatin, delaviridine, bis-tetrahydrofuran ligands, and didanosine.

The pharmaceutical composition of the present invention may be formulated in the form of suppositories, tablets, films, patches, and gels for oral, buccal, nasal, ocular, and topical routes; as well as spray formulations, drops, dry powder, suspensions and the like. The composition may additionally be formulated as microparticles.

The method of the present invention comprises administering to a subject an effective amount of a pharmaceutical composition comprising a mucoadhesive compound. Within the scope of the present invention, said mucoadhesive compound may not necessitate the presence of ligand or chelator groups in order to capture and bind to toxins. The ability of such mucoadhesive compound may rise from structural characteristics such as folding of the compound in the mucus layer thereby capturing the toxin irreversibly, the presence of pockets or cavities within the folded polymer, which may trap the toxin irreversibly, low-attraction forces etc.

Without wishing to be bound by theory, the removal of toxins from a mucosal membrane may take place as follows: upon application of the composition comprising the mucoadhesive compound, the buccal liquid e.g. saliva or nasal liquid or any other fluid which covers the treated mucosal membrane, penetrates into the composition and hydrates the mucoadhesive polymer, leading to the formation of a matrix. Such buccal liquid, which may contain the toxins, come into contact with the matrix of the mucoadhesive ligand, and progressively become bonded or attached thereto. The mucoadhesive agent may than be expelled from the mucosal membrane due to one or more of the following possible occurrences: (1) due to loading with the toxin, the ligand's mucoadhesivity reduces and it becomes detached from the layer or due to release of reversibly chelated ligand D (as described hereinbefore) which creates changes in the environment of mucoadhesive polymer reducing polymer's mucoadhesive properties; (2) it is no longer retentive; (3) it is expelled with the secretion of the mucus from the mucus glands; (4) it may be physically withdrawn from the mucus layer, e.g. by a tooth brush; (5) it may be absorbed into the blood system and expelled through the urinary or GI tract; (6) it may be vigorously washed off; (7) it may be biodegradable; or (7) in case of the nose and respiratory system it may be removed therefrom by sneezing and/or coughing.

Example 1

Figure 3:
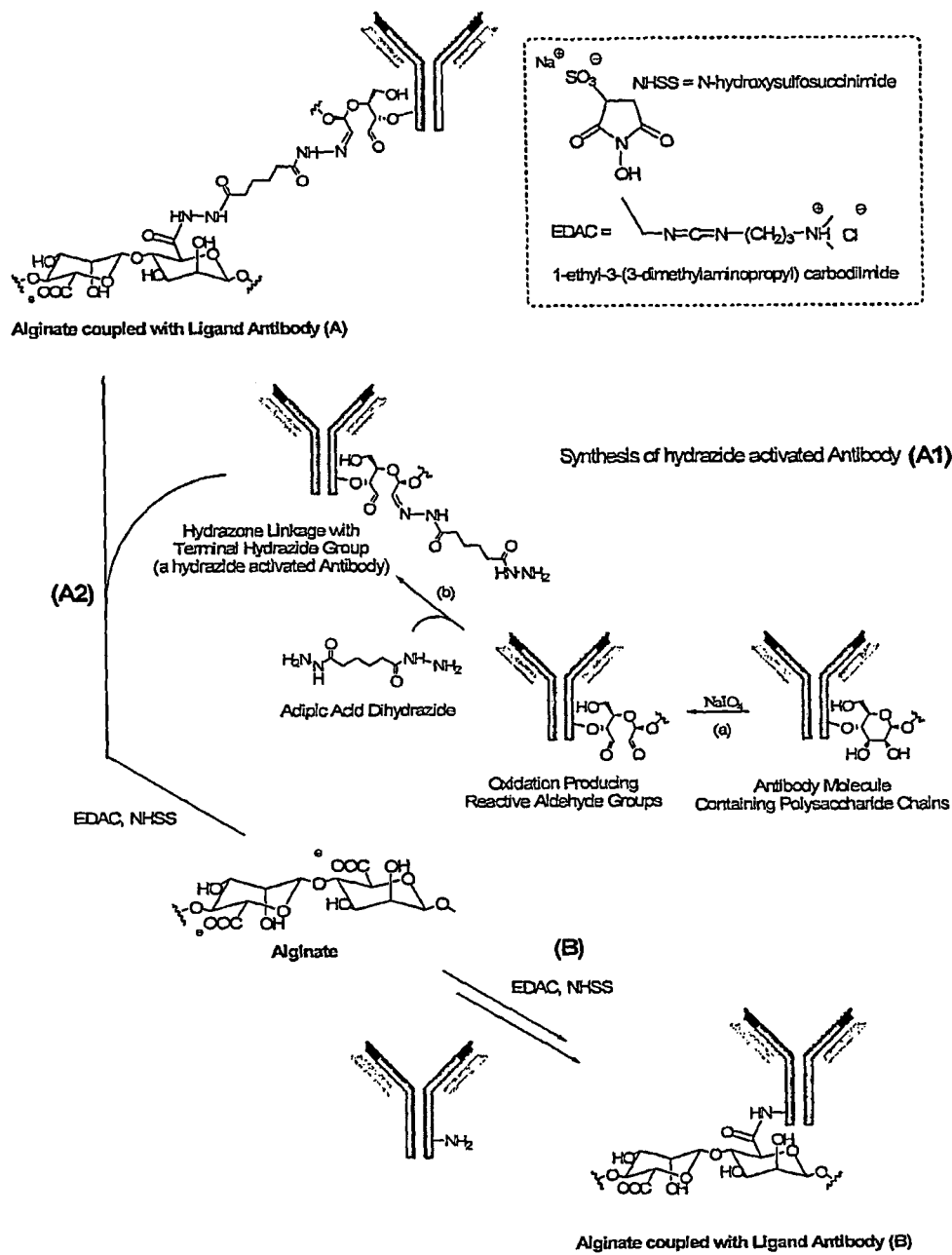
FIG. 3 depicts the synthetic strategy to couple alginate with different antibody to trap pathogenic biological entities.

Preparation of Oxidized Antibody (FIG. 3, step A1(a))

The antibody to be periodate-oxidized is dissolved at a concentration of 10 mg/ml in 0.01 M sodium phosphate, 0.15 M NaCl, pH 7.2. Sodium periodate is dissolved in water to a final concentration of 0.1 M and protected from light. Immediately thereafter 100 μl of the sodium periodate solution are added to each milliliter of the antibody solution and allowed to react in the dark for 30 min at room temperature. The oxidized antibody is purified by gel filtration using a column of Sephadex G-25. The chromatography buffer is 0.1 M sodium phosphate, 0.15 M NaCl, pH 7.2. To obtain efficient separation between the oxidized antibody and excess periodate, the sample size applied to the column should be at a ratio of no more than 5% sample volume to the total column volume. Collect 0.5-ml fractions and monitor for protein at 280 nm. Pool the fractions containing protein. Adjust the antibody concentration to 10 mg/ml for the conjugation step. The oxidized antibody should be used immediately.

Example 2

Coupling of Oxidized Antibody with Adipic Acid Dihydrazide (FIG. 3, step A1(b))

Dissolve a macromolecule (such as a protein/antibody) containing aldehyde functional groups (obtained in previous step) in a buffered solution at a pH of about 7-8.5 and at a concentration of about 1-10 mg/ml. Phosphate, carbonate, borate, or similar buffers adjusted to this pH range work well. Avoid amine-containing buffers (i.e., glycine or Tris) or other components containing strong nucleophiles, since these may react with the aldehydes. Higher pH environments enhance the formation of hydrazone bonds and generally increase the yield of complex. Add a quantity of adipic acid dihydrazide (Aldrich) to the protein (antibody) solution to obtain at least a 10-fold molar excess over the amount of aldehyde functional group present. If the concentration of aldehydes is unknown, the addition of 32 mg adipic acid dihydrazide per milliliter of the protein solution to be modified should be used. React for 2 h at room temperature. Although hydrazone formation does not require the addition of a reductant to create a linkage, including sodium cyanoborohydride (NaCNBH$_3$) in the reaction mixture considerably increases the yield and stability of bonds formed. If the presence of a reducing agent will not cause harm to the macromolecule being modified, the addition of 10 μl of 5 M sodium cyanoborohydride (Sigma) per milliliter of reaction solution may be done. Purify the modified protein (antibody) by dialysis or gel filtration. Hydrazide-activated proteins are stable to long-term storage at 4° C. in the presence of a preservative (0.05% sodium azide) or in a frozen or lyophilized state.

Example 3

Coupling of Hydrazide Activated Antibody to Alginate (FIG. 3, Step A2)

Dissolve 50 mg of hydrazide activated antibody in 1% (w/v) solution of alginate (20 ml solution, 1.0 mmol alginate monomer) in 0.1 M MES buffer, pH 6.0. Then, add 0.0216 g (0.1 mmol) of NHSS and 0.0384 g (0.2 mmol) of EDAC (ratios of reagents were calculated for a theoretical 20% molar modification of the number of carboxylic groups of alginate). React for 3 h at room temperature and purify the final product by reversible precipitation of alginate by decreasing the pH up to 3. The precipitate was collected by centrifugation, washed with water and then resolubilized in 0.1 M MES buffer. Alternatively, removal of non bound-antibody was accomplished by precipitating the alginate with 1% calcium chloride solution. The precipitate was collected by centrifugation, washed with water and resolubilized by addition of 0.1M Tris buffer pH 7.5 and a sufficient amount of 0.4M sodium citrate pH 6.3 to permit complete solubility.

Alternatively, alginate can be first modified with adipic dihydrazide using EDAC/NHSS activation of alginate and 10 molar excess of dihydrazide to prevent alginate self-crosslinking. The hydrazide activated alginate could be purified by dialysis. Then, sodium periodate oxidized antibody (described above) could be coupled to alginate by forming the hydrazone bonds. The final product will be purified by reversible precipitation as described above. $^{13}$C NMR and FTIR spectroscopy could be used to confirm the hydrazide activated alginate. The final antibody modified alginate could by analyzed using absorption method at 280 nm for protein content determination, ELISA or colorimetric protein determination method (Micro BCA™ Protein Assay Kit, cat. number 23235, Pierce) as well.

In the second approach, alginate could be coupled directly with antibody via carbodiimide chemistry as shown in FIG. 3, step B). In this case antibody is coupled through its amino groups to alginate backbone. The purification of antibody-modified polymer could be performed as described above.

Example 4

Preparation of Biotin-Conjugated Alginate in Aqueous Media

Figure 2A:
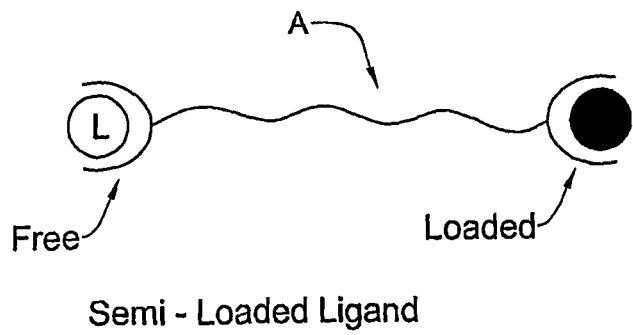
FIGS. 2A-C are schematic representations of free, semi- or fully loaded mucoadhesive ligands (A=mucoadhesive backbone; B=ligand or chelating group; and L=chelation cavity).
Figure 2B:
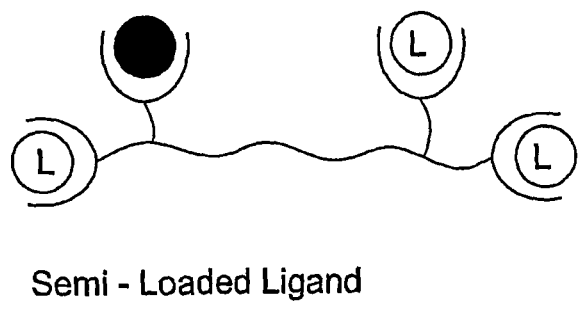
Figure 2C:
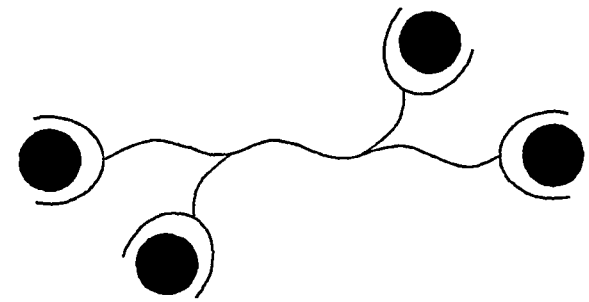

The biotin-alginate conjugate was prepared as shown in FIG. 2, step A. An amount of 0.052 g (0.2 mmol) of biotin hydrazide was added to a 1% (w/v) solution of alginate (20 ml solution, 1.0 mmol alginate monomer) in 0.1 M MES buffer, pH 6.0. The reaction mixture was stirred at room temperature for 60 min to facilitate a homogeneous dispersion of the biotinylating reagent in the reaction solution. Then, 0.0216 g (0.1 mmol) of NHSS and 0.0384 g (0.2 mmol) of EDAC were added (ratios of reagents were calculated for a theoretical 20% molar modification of the number of carboxylic groups of alginate). After 3 h at room temperature, the resulting polymer was dialyzed against doubly deionized water using a 10,000 MWCO membrane (66410, Rockford, USA). The water was changed twice a day for three days, after which time the modified alginate was lyophilized.

Spectroscopic Analysis

For FTIR spectroscopy, polymer samples were prepared as thin films as follows: 4 mg/ml of the modified alginate was dissolved in doubly deionized water. The resulting solution was poured into a polystyrene Petri dish and dried in an oven at 50° C. for 24 h to produce a thin transparent polymer film.

Quantitative Assay of the Extent of Biotinylation of the Alginate

A fluorescence-based method was used to determine the available biotin content in the modified alginate. In the presence of avidin, the fluorescence of 2,6-ANS is blue shifted (from 463 to 422 nm) with a large increase in quantum yield. Biotin binding causes complete displacement of the bound fluorophore, with a concomitant quenching of the fluorescence. The fluorescence-based assay was adapted to a 96-well microtitration plate format. Volumes of 1 µL of a 2,6-ANS (6 mg/mL in DMSO) and 66 µL of avidin (2 mg/mL) were added to different volumes of biotin (0.1 mM) from 0 to 120 µL (in increments of 10 µL) in the wells of a microtitration plate. Each well was brought up to a total volume of 200 µL with PBS, pH 6.0. Biotin-alginate samples (1 mg/mL) in volumes from 2 to 20 µL (in increments of 2 µL) were then assayed to determine the amounts of biotin on the alginate available for complexing with avidin. The fluorescence was monitored at 320 nm (excitation) and 405 nm (emission) by a POLARStar Galaxy fluorimeter (BMG-labtechnologies GmbH, Germany). All solutions, except 2,6-ANS, were prepared in PBS at pH 6.0.

Example 5

Activation of Alginic Acid with N-Hydroxysuccinimide and DCC in Organic Media

A 1.20 g (10.4 mmol) N-hydroxysuccinimide (NHS, Mw=115 g/mol) and 50.0 mmol (8.80 g) Alginic Acid (176 g/mol of monomer unit) dissolved in 100-150 ml of dry N,N-dimethylformamide (DMF) in a dry Argon atmosphere. After addition of 2.06 g (10.0 mmol) N,N'-dicyclohexylcarbodiimide (DCC, Mw=206.33 g/mol) the solution stirred overnight at room temperature. The precipitated solid filtered off and the filter rinsed with DMF or Acetonitrile-Acetone (1:1), and the filtrate diluted with a mixture of petroleum ether (Merck, 40-60° C.) and Isopropanol (6:1). After 2 h at room temperature a crude product is expected to be recovered by filtration, redissolved DMF and recrystallized from Petroleum ether:Isopropanol (6:1) to yield white solid product after drying in vacuum. Analysis must be performed. This protocol for activation of alginate is useful if the next coupling step will be carried out in the organic media. This protocol can farther be used for obtaining aldehyde activated alginate for ligand protein coupling (using in the final step 10% Dimethylformamide (DMF) or dimethylsulfuoxide (DMSO) in aqueous media for preservation of ligand-protein activity. Additional use of this activation of alginate could be used for fluorescence labeling by BODIPY (Molecular Probes).

Example 6

Figure 4:
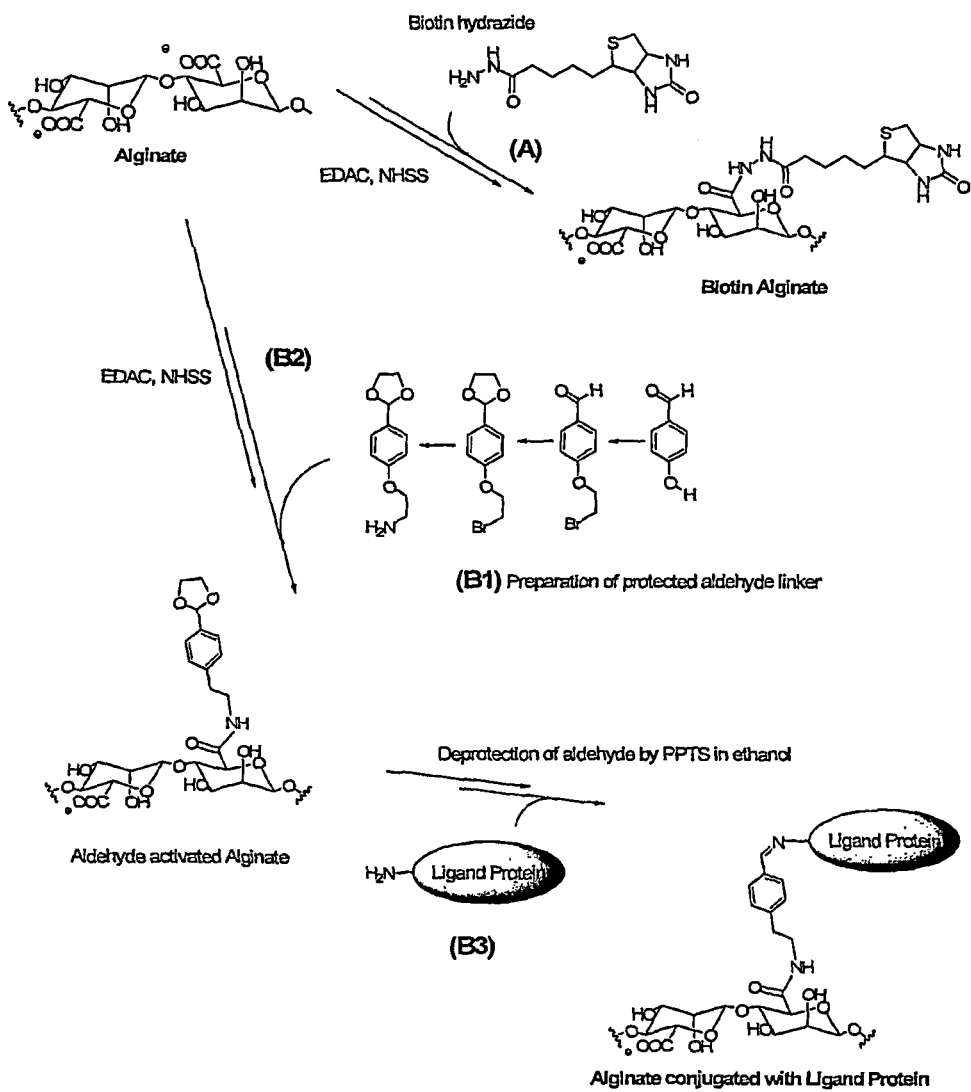
FIG. 4 depicts the synthetic strategy for producing an alginate conjugate with a ligand protein.

Preparation of Benzaldehyde Conjugated Alginate (FIG. 4, Steps B1-B3)

In order to prepare a benzaldehyde conjugated alginate, a few appropriate precursors are first synthesized. 4-(2-bromoethoxy)benzaldehyde is prepared by reacting p-hydroxibezaldehyde with 1,2-dibromoethane, in dry acetone. The product is then reacted with ethyleneglycol in toluene, with para toluene sulfonic acid as a catalyst, in dry conditions, in order to afford protection to the labile aldehyde groups. The protected 2-(4-(2-bromoethoxy)phenyl)-1,3-dioxolane is then reacted with potassium phthalimide, to afford 2-(4-(1,3-dioxolan-2-yl)phenoxy)ethanamine which is next coupled to the alginate using carbodiimide chemistry (using EDAC and NHSS as activators for alginate), as described previously. Then, the protecting group on the 1,3-dioxolane is removed by PPTS, in ethanol, and the free aldehyde is obtained. Any ligand protein may now be coupled by creating a Schiff base bond between the activated alginate and the amino group of the protein.

Example 7

Methods for the Quantification of the Extent of Alginate Modification with the "Ligand" Antibody or Determination of Binding Capacity of Modified Polymer 1. Direct Method—

Figure 5:
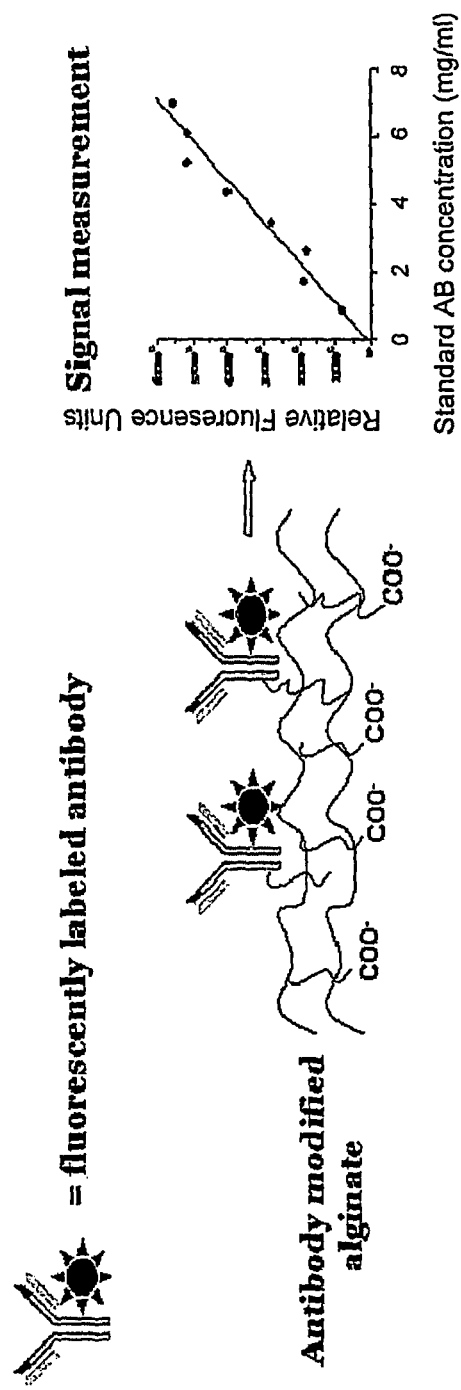
FIG. 5 shows the direct fluorescent assay for the quantification of the alginate modification.

To modify the alginate with fluorescently labeled antibody and to measure the fluorescence of modified alginate. The extent of alginate modification could be calculated from the calibration curve obtained from measurement of the fluorescence of standard solutions of fluorescently labeled antibody (FIG. 5).

2. Indirect Methods—

To conjugate the antibody modified alginate with its fluorescently labeled target virus and to measure the fluorescence of the bound virus. To perform this assay the alginate should be immobilized on the solid surface to allow blocking and washing steps before and after virus binding. The immobilization of alginate (polyanion) on the solid support could be achieved using polylysine (polycation) coated 96-well plates.

Figure 6:
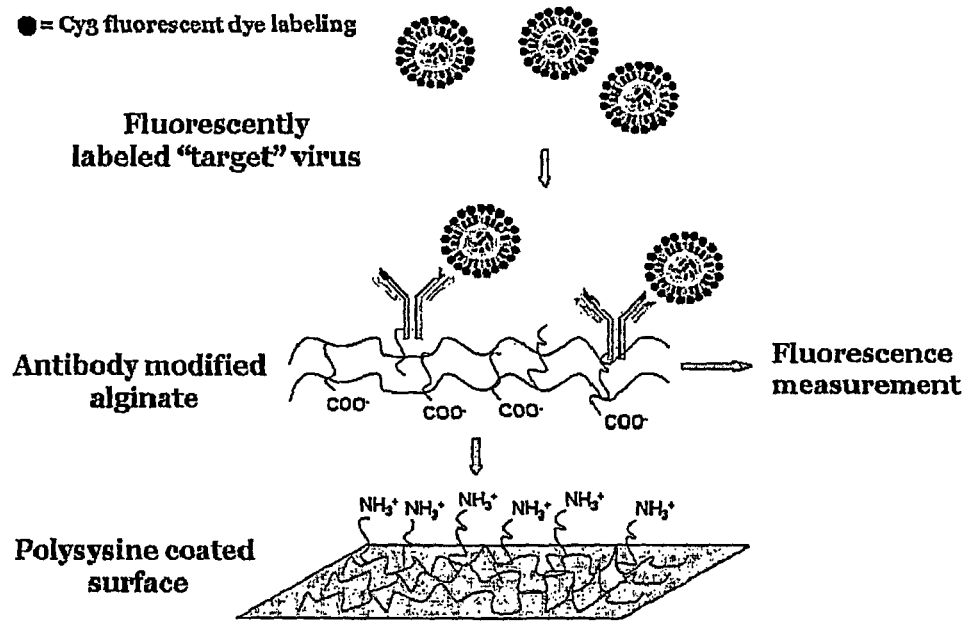
FIG. 6 shows the indirect assay for the quantification of the target virus binding capacity using fluorescently labeled virus.
Figure 7:
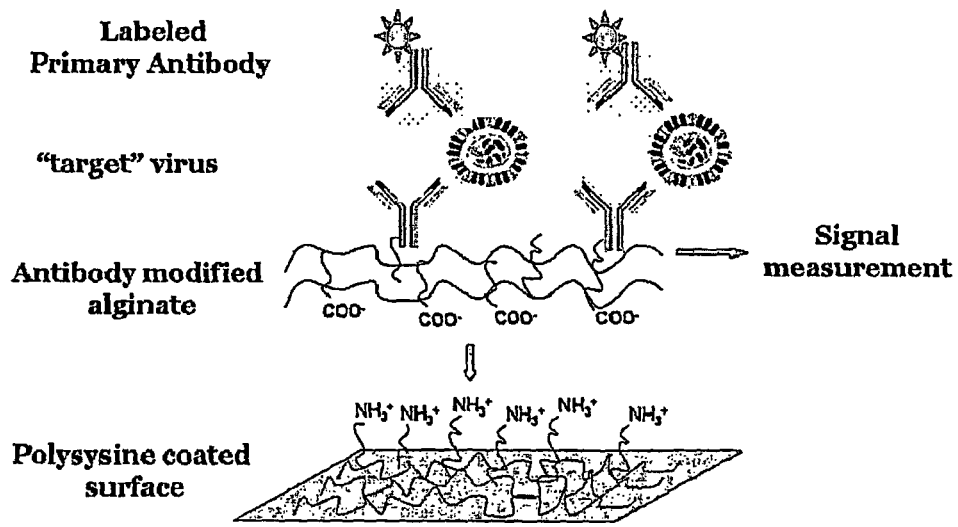
FIG. 7 depicts the ELISA assay for the quantification of the target virus binding capacity.
Figure 8A:
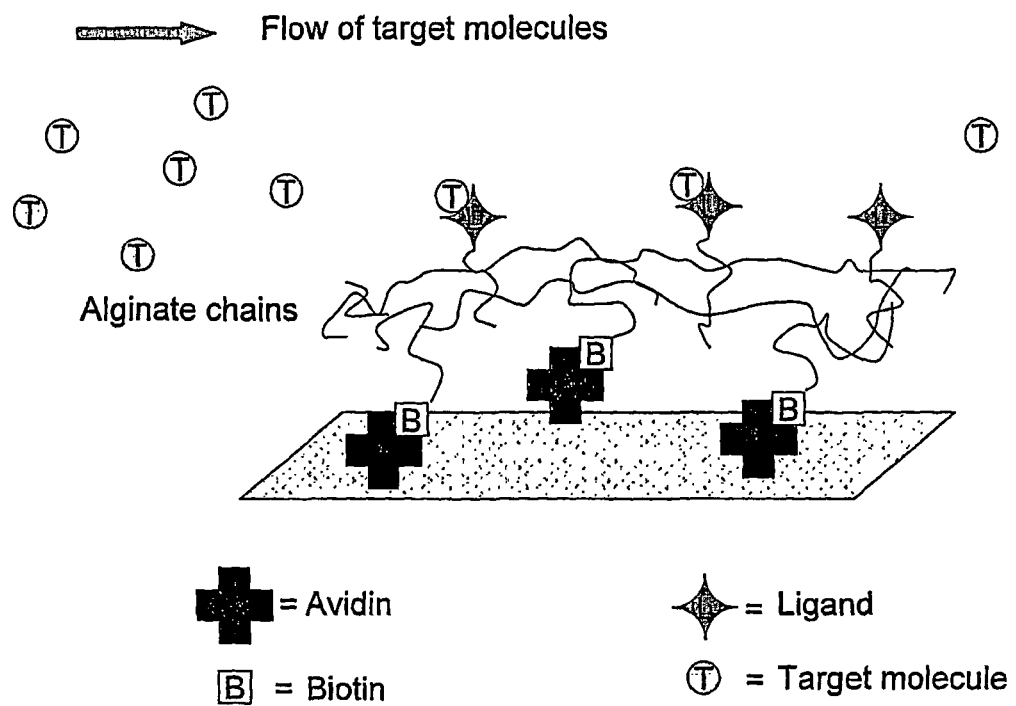
FIGS. 8A-B depict the kinetic study for the binding of the target molecule. (A) Immobilization of the conjugate of alginate with the ligand on the surface of the avidin coated slide, (B) binding kinetics using the fluorescent depletion method.
Figure 8B:
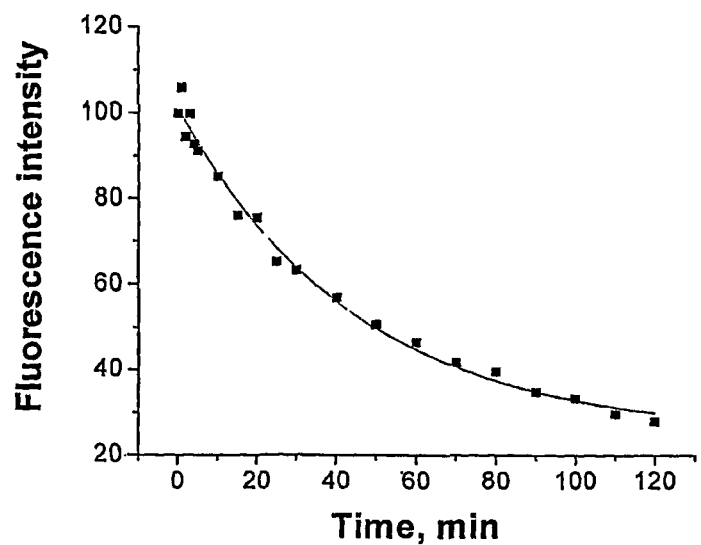
Figure 9A:
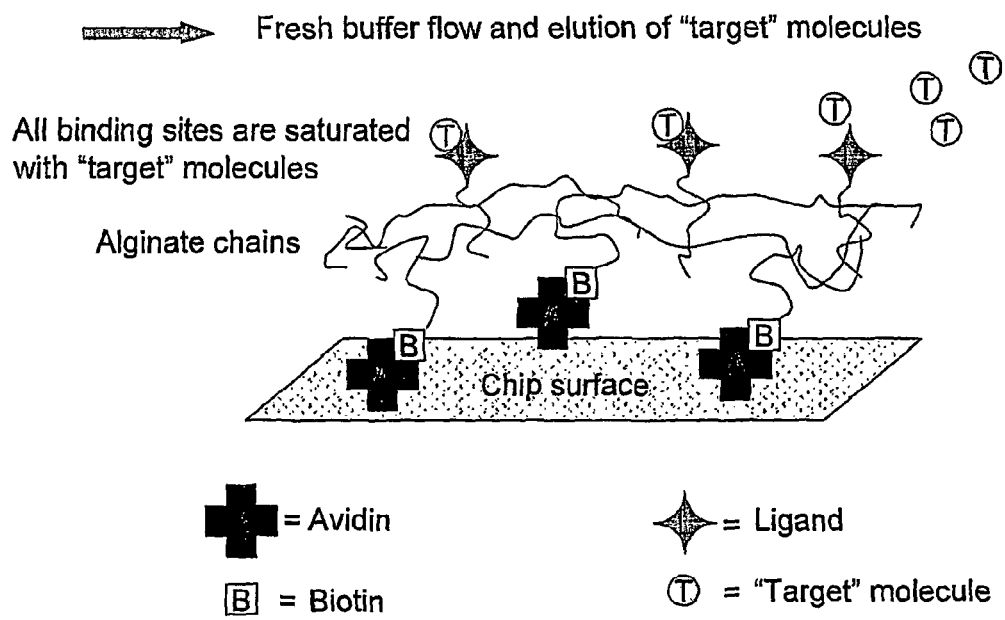
FIGS. 9A-B depict the kinetic study of the retention of the target molecule. (A) Immobilization of the conjugate of alginate with ligand on the surface of the avidin coated glass or gold coated slide, (B) binding kinetics study utilizing fluorescence the enrichment method.
Figure 9B:
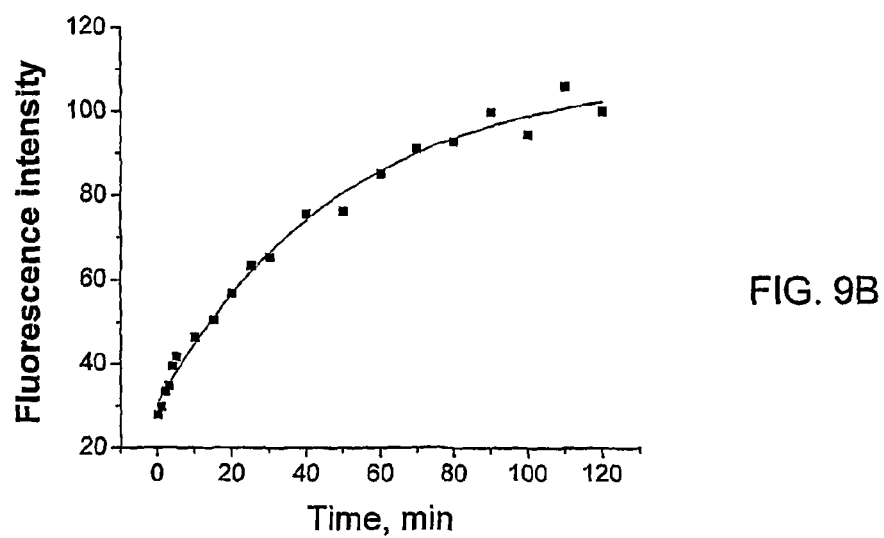

The mono/bis NHS-ester of Cy3 fluorescent dye (Amersham Biosciences Cat. No PA 23001/23000 can be used to fluorescently label the "target" virus (FIG. 6).

Alternative non-direct assay could be based on the sandwich ELISA principle. In the first step, to couple with antibody modified alginate its target virus. Then to introduce fluorescently labeled primary to target virus antibody. In that case also a calibration curve should be used to derive the extent of modification of alginate. Furthermore, this non-direct assay could allow calculating the real capacity of modified alginate to bind the "target" virus. In, that case, also a surface immobilization of alginate will be necessary. An alternative immobilization of alginate on the solid surface could be achieved using biotin modified alginate and avidin coated surface as summarized in the section describing the kinetic studies (FIG. 7).

Example 8

Binding Studies to Toxicants

For the binding and retention kinetics studies of various target entities the phenomenon of surface plasmon resonance (SPR) may be used to monitor the biomolecular binding events in real time without the use of labels.

In general, the refractive index change for a given change of mass concentration at the surface layer, is practically the same for all proteins and peptides, and is similar for glycoproteins, lipids and nucleic acids. Biomolecular binding events cause further changes in the refractive index and the SPR signal.

The kinetics of an interaction, i.e. the rates of complex formation ($K_a$) and dissociation ($K_d$), can also be determined as known to a person skilled in the art. The affinity of an interaction is determined from the level of binding at equilibrium (seen as a constant signal) as a function of sample concentration. Affinity can also be determined from kinetic measurements. For a simple 1:1 interaction, the equilibrium constant $K_D$ is the ratio of the kinetic rate constants, $K_d/K_a$. The extent to which different molecules interact with a single partner immobilized on a sensor surface reveals the specificity of an interaction. Simple yes/no answers are able to allow search for binding partners and performing of test for cross-reactivity.

For the kinetic studies, a dually modified alginate may also be used. First modification with biotin to the extent of 5-10% is necessary to link the alginate with the avidin coated chip surface. Second modification with appropriate ligand will be used for kinetic/affinity studies. The target molecule will flow over the chip surface interacting with the ligand immobilized on the chip (FIG. 8A). Alternatively, ligand modified alginate could be immobilized on the amino coated chip surface via carbodiimide chemistry using EDAC/NHSS activation for alginate.

Alternative binding/retention kinetic studies could be performed using fluorescently labeled target molecules. In that case, again dually modified alginate could be used. Avidin-biotin interaction allows for alginate immobilization on the surface of the glass/gold coated slides by means of silane/thiol chemistry. To obtain the kinetics data in that case the depletion (FIG. 8B) or the enrichment (FIG. 9B) of fluorescence of the "target" molecule in the solution flowed over the slide could be measured. For the retention studies, all binding sites of the alginate should be blocked or saturated with "target" molecule. Then, by passing fresh buffer to elute the "target" molecule the enrichment in fluorescence could be measured and retention kinetic could be determined.

Example 9

Gastric Juice Retention (Biodegradation) Studies

Preparation of Degradation Media—

Simulated gastric fluid (SGF) and simulated intestinal fluid (SIF) may be prepared in accordance with known procedures. Typically, the SGF is prepared by dissolving 2 g sodium chloride and 3.2 g pepsin (Sigma) in 7 mL hydrochloric acid and volume adjusted to 1 L by water to obtain a pH about 1.2. The SIF is prepared by dissolving 6.8 g of monobasic potassium phosphate in 250 mL of water. The solution is mixed and 190 mL of 0.2 N sodium hydroxide and 400 mL of water and 10 g of pancreatin (Sigma) are added. The pH then adjusted with 0.2 N sodium hydroxide to 7.5±0.1 and the volume completed to 1 L by water. Antibiotics such as Penicillin-streptomycin and antimycotic such as Fungizone may be added to each solution to avoid bacterial contamination.

Biodegradation Studies—

To study the biodegradation of ligand (antibody) modified alginate, a hydrogel microspheres may be prepared using the gas shear method, which employs a concentric air stream to shear the drop from the needle tip controlled essentially by the gas flow.

A 100 mg of dried microspheres are suspended in 5 mL of each medium (SGF and SIF) in 15 mL plastic tubes. Sample tubes are incubated at 37° C. under continuous shaking at 240 rpm. After a predetermined incubation time, the solution is filtered trough 0.45 mm Millipore nylon filter for HPLC and MALLS-SEC (multi-angle laser light scattering and size exclusion chromatography) analyses. Using HPLC analysis, the protein (antibody) degradation could be assessed. Using MALLS analysis, the carbohydrate degradation could be studied by measuring molecular weight distribution of the fragments of digested polymer.

Scanning Electron Microscopy (SEM)—

To determine the microspheres morphological and ultrastructural changes after incubation, scanning electron microscopy could be used. For SEM observations, incubated microspheres after degradation should be washed three times with DD water and stabilized with 3% glutaraldehyde solution in a 0.1 M phosphate buffer at 4° C. for 60 min. The microspheres then should be rinsed several times with the 0.1M phosphate buffer solution and post-fixed in 1% Osmium. Tetroxide ($OsO_4$) in a 0.1 M phosphate buffer at pH 7.2 for 24 at 4° C. After rinsing with water, the microspheres are dehydrated sequentially with increasing ethanol solutions concentrations (30, 50, 70, 90, 95 and 100 vol %). The ethanol-impregnated gel samples were totally dried by the critical point drying method (CDP). The dried samples fixed on aluminum sample holders using a silver-based adhesive and then coated by a conductive layer (15 nm) of Au/Pd (sputtering method).

Example 10

In Vitro Retention Strength Studies of Biopolymer (Mucoadhesion Studies)

Rheology as Means of Evaluating Polymer-Mucin Interactions—

This approach is, to some extent, based on the interdiffusion-interpenetration theory of the mucoadhesion process and, as such, aims to simulate the interpenetration layer between the gel and the mucus layer. When a putative mucoadhesive polymer is mixed with a mucin solution, there is a synergistic increase in viscosity. It is known that the viscosity of a polymer-mucin mixture should be considered to be the result of the contributions from the separate components, the polymer and mucin, and from a viscosity component arising from mechanical interactions (entanglements) and chemical interactions between the polymer and the mucin. For mucoadhesive polymers it is believed that the rheological response of a polymer-mucin mixture should be larger than the sum of the contributions from the gel and the mucin, a phenomenon that is commonly described as "rheological synergism".

The Synergism Parameters—

The most commonly used synergism parameter, $\Delta G'$, also called the interaction term, is the elastic component that is calculated from the equation $G'_{mix}=G'_p+G'_m+\Delta G'$, wherein $G'_{mix}$ is the elastic modulus of the polymer-mucin mixture and $G'_p$ and $G'_m$ represent the elastic modulus of the polymer and mucin respectively. This equation may be simplified because of the negligibly small elastic modulus of the mucin solutions at certain concentration range. Therefore, $\Delta G'$ could be calculated from: $G'_{mix}=G'_p+\Delta G'$.

Furthermore, the relative synergism parameter, which has been put forward as alternative to the absolute synergism parameter may be calculated from:

$$\text{Relative } \Delta G' = \frac{\Delta G'}{G'_p} = \frac{G'_{mix} - G'_p}{G'_p}.$$

A rheometric measurement normally consists of a strain (deformation) or a stress analysis at a constant frequency (normally 1 Hz) combined with a frequency analysis, e.g. between 0.1 and 100 Hz. The strain sweep gives information of the elastic modulus G', the viscous modulus G" and the phase angle. A large value of G' in comparison of G" indicates pronounced elastic (gel) properties of the product being analyzed. For such a product the phase angle is also small, e.g. 20° (a phase angle of 0° means a perfectly elastic material and a phase angle of 90° means a perfectly viscous material). The frequency sweep gives information about the gel strength where a large slope of the G' curve indicates low strength and a small slope indicates high strength.

A viscometric measurement normally consists of a shear rate analysis. The shear rate sweep should preferably cover the range applied in the intended equipment. For liquid samples a shear rate range from around 1 to 1,000 $s^{-1}$ covers the needs for a low-viscous materials and a shear rate range from around 1 to 100 $s^{-1}$ covers the needs for a high-viscous materials.

Tensile Strength Methods for Measuring the Mucoadhesion of Gels—

There are two ways by which the mucoadhesion of the compounds may be evaluated. In the first approach, the measurement configuration involved one piece of mucosa and a large volume of agent to be tested.

In the other approach, a relatively small volume of the agent is used and placed between two pieces of mucosa. In this method, the measurement started by lowering the upper mucosa until contact was made with the agent. After a certain contact time the upper mucosa was slowly withdrawn upwards at a constant speed until detachment occurred. During the entire measurement a force-distance curve was recorded from which the tensile work (i.e., the area under the curve during the withdrawal), the peak force and the deformation to failure were determined. As the mucosa is separated from the agent (preferably in a gellous form), failure will occur in the weakest of the three regions of the mucoadhesive complex: in the gel, in the mucus or in the interface layer between the gel and the mucus where it is possible that interactions strengthen the mucus layer. Consequently, the force-distance curve recorded in the measurement gives a measure of the strength of the bonds in the weakest region. To interpret the results and to determine the region in which failure occurs (i.e., which bonds are reflected in the acquired data), the cohesiveness of these components with the results from the mucoadhesion measurement should help to identify which region is the weakest. This procedure offers a good basis from which to asses whether the measured tensile work reflects a genuine interaction of the gel preparation with the mucus layer or the cohesive failure of the gel.

Alternative In-Vitro Mucoadhesion Studies—

Another method to measure of mucoadhesive properties of modified alginate microspheres is by determination of the quantity of microspheres sticking to a filter paper saturated with mucin and after applying an air load. The air jet can be used to simulate breathing in and out. It could be useful to evaluate the effect of air-flow on nasal clearance of micro particulate formulations after their administration.

Example 11

In Vivo Feasibility Experiment to Trap the Model Pathogen-Adenovirus (AdV) Aerosolized into Mouse/Rat Oral Cavity Pre-Coated with Adhesive Bio-Hybrid Polymer-Alginate The purpose of alginate modification with anti-AdV antibody is to provide the alginate the ability to bind free adenovirus (AdV). The purpose of alginate modification with cystein or wheat germ agglutinin lectin (WGA) is to provide the alginate with improved mucoadhesive properties for better retention of the polymer on mucoadhesive tissue, e.g. in the mouth cavity (buccal cavity) and larynx or upper throat.

Alternatively, two mono-modified alginates can be used in mixture: Alginate modified with AdV antibody or Alginate modified with cystein/lectin (WGA). The mixture of alginates may be used to obtain conceptually similar properties (affinity to AdV and improved mucoadhesive ability) as could be achieved by dually modified alginate described above.

Alternatively, mono-modified alginate with anti-AdV antibody as initial test without the enhancing the mucoadhesive properties may also be tested.

The mucoadhesive polymers of the invention may be cross-linked in situ after administration to the target membrane. In such an approach, the polymer is aerosolized (sprayed) in the mouth cavity and the upper respiratory tract in an anesthetized animal. This forms the initial film of non cross-linked polymer solution in the buccal cavity and the respiratory tract. Immediately thereafter, a solution of crosslinker is sprayed in the mouth cavity and respiratory tract of animal. In this way, the deposited polymer(s) is crosslinked on the interior oral cavity surface creating biohybrid hydrogel coating. The additional number of hydrogel layers could be created on the base of the first hydrogel layer by the same repeatable manipulations: spraying of additional polymer dose and a consequent spraying of the crosslinker reagent to harden the gel. The purpose of few layers is to create a homogeneous coating in the oral cavity of the animal. The number of polymer layers may be determined experimentally.

The capturing of the AdV may be tested as follows: The control and the experimental groups (pre-coated with non-functionalized alginate and functionalized alginates respectively) of mildly anesthetized animals are exposed to the AdV spray (aerosol) using Nebuliser. Additional animal control groups are: (1) animal without protective polymer coating exposed to the same AdV dose, (2) non-treated animals without the gel pre-coating and without the exposure to AdV and (3) pre-coated animals with protective polymer but not exposed to AdV. Control (2) and (3) will allow to determine the background fluorescence of the non treated animal and effect of gel on animal respectively.

Both the time of exposure to AdV and the appropriate viral titer are determined experimentally. 24-48 hours post exposure to AdV, the animals are imaged non-invasively using an imaging system.

In addition, to follow up after the expression of reporter genes encoded by AdV it is also possible to track the AdV localization in the animal by using fluorescently labeled AdV, using for example the mono/bis NHS-ester of Cy3 fluorescent dye. Tracking of AdV in animal could be assessed using non invasive imaging mentioned above or fluorescent microscopy.

Example 12

Mouse Lung Lavage: Determination of the Persistence of Hydrogel in the Lungs

Mice are killed by $CO_2$ suffocation by placing them in a jar containing dry ice. The asphyxiated mouse is then placed on its back and its ventral side is swabbed with ethanol. A midline ventral incision is made and the fur stretched away from the abdomen to the mandible, uncovering the muscle layer. The sternohyoid and throat muscles are teased apart; the trachea is exposed and left in-situ. The thoracic cage is partially removed to uncover the intact lungs. A thread is placed just under the trachea and both sides of it are used to slightly pull the trachea up. A Venflon® I.V. Cannula is inserted into the trachea towards the lungs within 5 mm of the larynx. The injection valve is slowly pulled out leaving the Teflon catheter inserted. The cannula is firmly secured to the trachea with single knot to avoid leakage and then attached to a three-way stopcock, previously connected to two syringes, one empty and the other containing BSA/PBS. Two to three flushes are used to rinse the inflated lungs and the aspirated bronchial secretions are drawn into the other syringe. The collected bronchoalveolar lavages are pooled, dispensed into aliquots, and then stored at $-20°$ C. until assayed. If needed, serum can also be obtained by cutting a nearby artery and the heart. Just before use, the washings are centrifuged to remove cellular debris and pooled samples containing erythrocytes are discarded.

Example 13

Ligated Ileal Loop: Protective Capacity of the Bioaffinity Hydrogel Linked with Anti-Cholera Toxin Antibodies Anesthetized postweaned rabbits (4-8 months old, 1-2 kg) are put on a liquid diet 48 h prior to the challenge assay. A 100 cm piece of small bowel beginning just above the appendix is exposed and kept moist while experimental (6 cm) and spacer (2 cm) loops are tied. Fully enteropathogenic *Vibrio* cholorae strain 395 is slowly injected into the large loops in ten-fold serial dilutions with PBS as a control. A second tie is made to isolate the site of injection. Before closing the abdomen in one layer with a running stitch, 5% glucose is given i.p. to reduce postoperative dehydration and the skin is then clipped shut. Food is not made available after the operation but water is supplied ad Libitum. The rabbit is killed after 18-20 h. Pictures are taken of the dissected small intestine containing the loops, and labeled according to contents and anatomy. Leakage between positive and negative loops is checked by injecting Pontamine sky blue 6 BX. Negative loop reactions are indistinguishable from normal collapsed bowel, while the positive loops are elongated and distended with fluid containing flecks of mucus, vibrios, enterocytes and other biological material. The fluid accumulation is measured by liberating the turbid contents from the tightly distended sacs.

Example 14

IVIS—Nasal to GI Tracing of a Hydrogel Preparation in Mice using IVIS System

15 Balb/C mice (8-10 weeks old) will be put on a chlorophyll free diet 72 h prior to the challenge assay. The mice will be anesthetized and fur removed (by shaving or depilation) and the mice will be divided into 5 groups. Group C (calibration) will be anesthetized. Then a calibration test will be conducted for the purpose of determining the right concentration of Cy7-avidin to be detected by the IVIS system. Each of the other groups will be anesthetized and will be provided with different formulations through nasal instillation and then will be examined using the IVIS system: Group I will be provided with the buffer solution (solvent), Group II will be provided with Cy7-avidin, Group III will be provided with conjugated alginate biotin, Group IV will be provided with conjugated alginate-biotin bound to Cy7-avidin. The concentrations will be determined by the calibration assay (group C). The mice will be detected by the IVIS imaging system, three mice at a time. All animals will be euthanized by respiratory exposure to excess $CO_2$.

Example 15

Toxin Challenge Model: Demonstration that Bioaffinity Hydrogel is Protective Against a Model Toxin 40 Balb/C mice (8-10 weeks old) will be divided into four groups, with two sub-groups in each group. The animals will be provided through nasal instillation with *staphylococcus* enterotoxin B, dissolved in sterile pyrogen-free phosphate buffered saline. Group I will be provided with only buffer solution (control), group II will be provided with 0.25 μg toxin per every gram of the mouse weight, group III—0.75 μg/gr, group IV—1 μg/gr. All the instillations will be provided by the equation of 1.5 μl/gr. Every sub group will be euthanized 24 h after the instillation by respiratory exposure to excess $CO_2$. Airway lavage will be performed in the euthanized animals, and the number of inflammatory cells will be counted. The other sub-group will be supervised over four days, to test the influence of the toxin. The animals will be weighed every day during the supervision. Clinical signs like hypothermia, inactivation and loss of more than 20% in body weight, will be watched for 2-3 times a day. The schedule of the sacrifice may be brought forward if the animal shows clinical signs of severe ill health, before the determined euthanasia of 96 h after the toxin exposure. All animals will be euthanized by respiratory exposure to excess $CO_2$. Airway lavage will be performed in animals euthanized 96 h after toxin administration and the number of inflammatory cells will be counted.

Example 16

In Vivo Studies: Challenge Studies with Virus

40 Balb/C mice (8-10 weeks old) will be divided to four groups, with four sub-groups in each group. The animals will be provided through nasal instillation with influenza virus. Group 1 will be provided with only buffer solution (control), group 2 will be provided with 0.25 μg toxin per every gram of the mouse weight, group 3 with 0.75 μg/gr, group 4 with 1 μg/gr. All the instillations will be provided by the equation of 1.5 μl/gr. Every sub group will be euthanized 24 hours after the instillation by respiratory exposure to excess $CO_2$. Airway lavage is performed in animals euthanized, and the number of inflammatory cells is counted.

The other sub-group will be supervised over four days, to test the influence of the toxin. The animals will be weighed every day during the supervision. Clinical signs like hypothermia, inactivation and loss of more than 20% in body weight, will be observed 2-3 times a day. The schedule of the sacrifice might be brought forward if the animal shows clinical signs of severe ill health, before the determined euthanasia of 96 hours after the toxin exposure.

At the time of the scheduled sacrifice, all animals will be euthanized by respiratory exposure to excess $CO_2$. Airway lavage is performed in animals euthanized 96 hours after toxin administration and the number of inflammatory cells is counted. Similar and appropriate protocols will be followed for the instillation of rats with Rift Valley fever and of guinea pigs with Marburg virus.

Example 17

Immobilization of Pollen and Viruses in a Hydrogel Composed of Alginate Bio-Conjugated to Macromolecules with Non-Specific Affinity and Adhesion Properties to Pollen and Viruses Flowering plants possess in the female organs of the flower specialized extracellular matrices that support pollen tube growth and sperm cell transfer along the transmitting tract of the gynoecium. Transport of the pollen tube cell and the sperm cells involves a cell adhesion and migration event, in species such as lily that possesses a transmitting tract epidermis in the stigma, style, and ovary. A bioassay for adhesion was used to isolate from lily stigma/stylar exudate the components that are responsible for in vivo pollen tube adhesion. At least two stylar components are necessary for adhesion: the first being a large molecule and the second being a small (9 kD) protein (Stigma/stylar cysteine rich adhesion, SCA). In combination, the two molecules induced adhesion of pollen tubes to an artificial stylar matrix in vitro. The 9-kD protein was purified, and its corresponding cDNA was cloned. This molecule shows some similarity with plant lipid transfer proteins. Immunolocalization data support its role in facilitating adhesion of pollen tubes to the stylar transmitting tract epidermis.

1) Isolation of Lily Stylar Exudates:

Easter lily (*Lilium longiflorum* Thumb cvs. Snow Queen and Nellie white) flowers should be collected 1-2 days after anthesis. The pollen grains should be used immediately or dried at room temperature overnight then stored at −80 degrees Celsius for further use. The stigma exudate should be collected from the cut stigma by incubation with an extraction buffer (see below). The stylar exudates should be eluted by two different methods. Lily styles should be collected and the stigma and ovary should be removed. In one method, after removing the stigma and ovary the stylar exudate should be eluted from the hollow style by applying extraction buffer (84 mM citric acid, 2 mM Na2S2O4, pH 3) to the top (the stigma position) of the style and collecting exudate from the bottom (the ovary position). These exudates should be dried by speed vacuum or lyophilization and stored at −20 degrees Celsius for further characterization. A second method can be used: The stigma and ovary of the lily gynoecium should be removed and the style bisected longitudally to expose the transmitting tract tissue.

Stylae Segments of Lily gynoaeum 2-3 days after anthesis should be incubated with the same extraction buffer for 2 hours at 4 degrees Celsius with gentle shaking the element should be centrifuged at 6000 g for 10 min. to remove cell and/or tissue debris. The eluted stylar exudates should be dialyzed against water with Spectra/Por dialysis membrane tubing (MWCO 12,000-14,000, Spectrum, Houston, Tex.) for 2 days with at least four changes of water. After dialysis the stylar exudates should be lyophilized and stored at −20 Degrees Celsius separately for further characterization and fractionation.

2) SDS-Polyacrylamide Gel Electrophoreses:

The crude lily stylar samples collected by two different methods should be mixed with an equal amount of 2×SDS sample loading buffer [100 mM Tris (pH 6.8), 100 mM beta-mercaptoethanol, 4% (w/v) SDS, 0.2% (w/v) bromophenol blue, and 20% (v/v) glycerol], boiled for 5 min and fractionated by 12% SDS-poly-acrylamide gel electrophoresis (SDS-PAGE). Gels should be run for 10 hours at a constant voltage (50V), fixed either stained with silver or with 50 mM (beta-D-glucosyl), Yariv phenylglycoside [(beta-D-Glc), Yariv reagent in 1% NaCl overnight. Cut relevant fraction of the 9 kD lily exudate protein and extract the protein fraction. Use Sephadex G200 column performing fractional collection with the appropriate buffer. Concentrate the 9 kD lily exudate protein fraction using Speed-Vac® system.

3) Preparation of Alginate-N-oxy-succinimide:

1.20 gm (10.4 mmol) N-Hydroxy-succinimide (NHS) and 10.0 mmol (xgm) Alginic Acid were dissolved in 25 ml of dry DMF in a dry Argon atmosphere. After addition of 2.26 g (11.0 mmol) dicyclohexyl carbodiimide (DCC) the solution was stirred overnight at room temperature. The precipitated solid was filtered off and the filter rinsed with 5 ml DMF or 5 ml Acetonitrile-Acetone (1:1). Next, the filtrate was diluted with 180 ml of a mixture of petroleum ether and isopropanol (6:1) and after 2 hours at room temperature, a crude product was recovered by filtration, re-dissolved in 5 ml DMF and recrystallized from Petroleum ether:isopropanol (6:1) to yield 2.8 mmol, 28% product as a white solid after drying in vacuuo.

The conjugates should be generally synthesized in 10 microliter reactions containing 2.4 mM of the Water lily 9 kD exudate protein analogue, 0.1M of the respective N-Hydroxy Succinimide activated Alginate, 0.4M $K_2HPO_4$ (pH 8.0) and 20% DMF at room temperature. After 2-3 hours the reactions should be quenched with 2 microliter ammonium acetate (1 M) for 30 min. diluted to 100 microliter. Dialysis should then be performed. Reconstitution or mixing of the Alginate-9 kD protein conjugate with lily exudate for the other component responsible for adherence for forming and evaluation of the Hydrogel should be performed and Adhesion properties of Lilly Pollen in Vitro should be performed.

4) Attempt of Conjugation Coupling Reaction Between the Purified 9 kD Lily Protein from Exudate and N-Hydroxy Succinimide Activated Alginate The conjugates should be generally synthesized in 10 microliter reactions containing 2.4 mM of the Water Lily 9 kD exudate protein analogue. 0.1M of the respective N-Hydroxy-Succinimide activated Alginate 0.4M $K_2HPO_4$ (pH 8.0) and 20% DMF at room temperature. After 2-3 hours the reactions should be quenched with 2 microliter ammonium acetate (1M) for 30 min. diluted to 100 microliter Dialysis should then be performed Reconstitution or mixing of the Alginate-9 kD protein conjugate with Lily exudate for the other component responsible for the adherence for forming and evaluation of the Target Hydrogel should be performed and Adhesion properties of Lilly Pollen in Vitro should be performed.

5) In Vitro Adhesion Assay of Lily Pollen

Pollen from different anthers suspended in 20 mL of germination medium, which resulted in an estimated 125,000±17,000 pollen particles. Several 28-$mm^2$ Petri dishes were coated with a thin layer (hydrogel layer) of Alginate-9 kD protein (stigma/stylar cysteine-rich adhesin (SCA)) conjugate from Lily exudates (experimental sample) and non-modified alginate (control sample), and the 20 mL of pollen suspension was then added. After short incubation of 10-15 min, the pollen containing medium aspirated and the alginate films washed by fresh germination medium (supplemented with calcium chloride 0.05M) three times at least. The actual number of pollen particles that adhered to the 28-$mm^2$ surface of Petri dish coated with experimental and control polymer gels was counted with a stereomicroscope after the polymer gel film was stained with Coomassie blue (protein staining).

6) In Vitro Binding Assays Between SCA Protein and Alginate

Stigma/stylar cysteine-rich adhesin isolated from the stigma exudate (SCA [SE]) (5 mg) and 50 mg of a carbohydrate polymer (alginic acid) were combined at pH 6.0 or 10.0. After 15 min of incubation at room temperature, the mixture (55 mL) was diluted with 1 mL of 100 mM Tris-HCl buffer, pH 6.0 or 10.0, and passed through a Centricon filter (molecular mass cutoff of 100 kD; Millipore, Bedford, Mass.). After being rinsed four times with 1 mL of buffer each, the retentate and the filtrate were collected and concentrated by vacuum centrifugation. The dry residues (retentates and filtrates) were resuspended with an identical volume of SDS buffer (50 mL) to allow quantitative comparisons, and 10 mL of each suspension was loaded on 12.5% SDS—polyacrylamide gels. For a control, SCA (5 mg) only was passed through the 100-10 Centriconfilter. The interaction pattern between SCA protein and alginate is analyzed from the SDS-poyacryamide gel results.

The invention claimed is:

1. A method for binding pollen at a mucosal membrane or in the environment thereof, comprising contacting a mucosal membrane of a subject with an effective amount of a composition comprising at least one compound of the formula A-$(B)_n$, wherein A is alginate, which can adhere to the mucosal membrane, B is an antibody that is chemically substituted onto A and is capable of specifically binding to the pollen, and n is the number of ligand groups substituted onto A, said number being greater than or equal to 1.

2. The method according to claim 1, wherein n is between 1 and 10.

3. The method according to claim 2, wherein n is between 1 and 5.

4. The method according to claim 2, wherein n is 1, 2 or 3.

5. The method according to claim 1, wherein the mucosal membrane is in a living animal.

6. The method according to claim 5, wherein said living animal is a human.

7. The method according to claim 1, wherein the mucosal membrane is a membrane of the mouth, gastrointestinal tract (GI tract), nose, nasal cavity, lungs, larynx, trachea, pharynx, vagina, rectum or urethra.

8. The method according to claim 7, wherein the mucosal membrane is related to the respiratory system.

9. The method according to claim 8, wherein said respiratory system is the upper respiratory system.

10. The method according to claim 1, wherein said contacting step is by topical administration.

11. The method in accordance with claim 1, wherein said mucosal membrane is in a subject having an allergy and said pollen causes an allergic reaction in the subject.

* * * * *